(12) United States Patent
Casqueiro et al.

(10) Patent No.: US 10,368,842 B2
(45) Date of Patent: Aug. 6, 2019

(54) ESTIMATION OF ACOUSTIC LEVEL IN-SITU WITH NON-FUNDAMENTAL ANALYSIS

(71) Applicant: Bracco Suisse S.A., Manno (CH)

(72) Inventors: Gilles Casqueiro, Manno (CH); Emmanuel Gaud, Manno (CH); Marcel Arditi, Manno (CH); Peter Frinking, Manno (CH)

(73) Assignee: Bracco Suisse S.A., Manno (CH)

( * ) Notice: Subject to any disclaimer, the term of this patent is extended or adjusted under 35 U.S.C. 154(b) by 331 days.

(21) Appl. No.: 15/302,467

(22) PCT Filed: Apr. 3, 2015

(86) PCT No.: PCT/EP2015/097020
§ 371 (c)(1),
(2) Date: Oct. 6, 2016

(87) PCT Pub. No.: WO2015/155380
PCT Pub. Date: Oct. 15, 2015

(65) Prior Publication Data
US 2017/0027545 A1 Feb. 2, 2017

(30) Foreign Application Priority Data
Apr. 7, 2014 (EP) .................................. 14163716

(51) Int. Cl.
*A61B 8/08* (2006.01)
*A61N 7/02* (2006.01)
(Continued)

(52) U.S. Cl.
CPC ............ *A61B 8/481* (2013.01); *A61B 8/5269* (2013.01); *A61B 8/58* (2013.01); *A61N 7/02* (2013.01);
(Continued)

(58) Field of Classification Search
CPC ......... A61B 8/06; A61B 8/481; A61B 8/5269; A61B 8/58; A61N 7/02; A61N 2007/0039; A61N 2007/0052
(Continued)

(56) References Cited

U.S. PATENT DOCUMENTS 5,203,337 A 4/1993 Feldman
5,287,273 A 2/1994 Kupfer et al.
(Continued)

FOREIGN PATENT DOCUMENTS

CN 1977186 A 6/2007
CN 101128154 A 2/2008
(Continued)

OTHER PUBLICATIONS

International Searching Authority, "International Search Report and Written Opinion from PCT Application No. PCT /EP2015/097020", dated Jul. 23, 2015, pp. 1-17, Published in: WO.
(Continued)

*Primary Examiner* — Michael J Carey
(74) *Attorney, Agent, or Firm* — Fogg & Powers LLC

(57) ABSTRACT

A method is provided for use with an ultrasound scanner, wherein an estimate value (particularly, a power level of the ultrasound scanner that is required to apply a desired acoustic pressure level to the body-part, the acoustic pressure level that is actually applied to the body-part when a specific power level is set, an acoustic attenuation that occurs within a patient between a transducer of the ultrasound scanner and the body-part and/or the acoustic attenuation that occurs within the patient between different body-parts) is determined according to a comparison between measurement data (based on a measurement response comprising a non-fundamental component of a measurement echo signal received in response to a measurement excitation signal) and
(Continued)

corresponding reference data. Corresponding computer program product, system, therapeutic method, and diagnostic method are also provided.

25 Claims, 11 Drawing Sheets

(51) Int. Cl.
    *A61B 8/00*                 (2006.01)
    *A61B 8/06*                 (2006.01)
    *A61N 7/00*                 (2006.01)
(52) U.S. Cl.
    CPC .......... *A61B 8/06* (2013.01); *A61N 2007/0039* (2013.01); *A61N 2007/0052* (2013.01)
(58) Field of Classification Search
    USPC ........................................................ 600/431
    See application file for complete search history.

(56) References Cited

U.S. PATENT DOCUMENTS

| | | | |
|---|---|---|---|
| 5,583,902 | A | 12/1996 | Bae |
| 5,833,613 | A | 11/1998 | Averkiou et al. |
| 6,216,094 | B1 | 4/2001 | Fox Linton et al. |
| 6,445,945 | B1 | 9/2002 | Arsenault |
| 6,540,680 | B1 | 4/2003 | Kurosaki |
| 6,676,606 | B2 | 1/2004 | Simpson et al. |
| 6,740,039 | B1 | 5/2004 | Rafter et al. |
| 6,879,853 | B2 | 4/2005 | Meaney et al. |
| 7,069,068 | B1 | 6/2006 | Oestergaard |
| 7,998,076 | B2 | 8/2011 | Phillips et al. |
| 8,409,103 | B2 | 4/2013 | Grunwald et al. |
| 8,512,249 | B2 | 8/2013 | Frinking et al. |
| 9,198,639 | B2 | 12/2015 | Frinking et al. |
| 9,307,957 | B2 | 4/2016 | Frinking et al. |
| 9,734,584 | B2 | 8/2017 | Frinking |
| 10,130,342 | B2 | 11/2018 | Frinking et al. |
| 2001/0021808 | A1 | 9/2001 | Shi et al. |
| 2003/0153823 | A1 | 8/2003 | Geiser et al. |
| 2004/0172303 | A1 | 9/2004 | Declerck et al. |
| 2007/0073146 | A1 | 3/2007 | Phillips et al. |
| 2007/0232909 | A1 | 10/2007 | Hughes et al. |
| 2007/0279500 | A1 | 12/2007 | Castorina et al. |
| 2007/0289500 | A1 | 12/2007 | Maeta et al. |
| 2008/0139942 | A1 | 6/2008 | Gaud et al. |
| 2009/0171215 | A1 | 7/2009 | Kato et al. |
| 2009/0253986 | A1 | 10/2009 | Frinking et al. |
| 2009/0304593 | A1 | 12/2009 | Frinking et al. |
| 2011/0015522 | A1 | 1/2011 | Arditi et al. |
| 2011/0188722 | A1 | 8/2011 | Huang |
| 2013/0006106 | A1* | 1/2013 | O'Reilly ................. A61N 7/02 600/431 |
| 2014/0243667 | A1* | 8/2014 | Wilkening ............... A61N 7/00 600/438 |
| 2018/0353158 | A1 | 12/2018 | Frinking et al. |
| 2019/0053791 | A1 | 2/2019 | Frinking et al. |

FOREIGN PATENT DOCUMENTS

| | | |
|---|---|---|
| CN | 101160097 A | 4/2008 |
| CN | 101305399 A | 11/2008 |
| CN | 101917908 A | 12/2010 |
| CN | 102223841 A | 10/2011 |
| CN | 102460506 A | 5/2012 |
| CN | 102483847 A | 5/2012 |
| EP | 0458745 | 11/1991 |
| EP | 0554213 A1 | 8/1993 |
| EP | 2189112 A1 | 5/2010 |
| JP | H08336531 A | 12/1996 |
| JP | H11164832 | 6/1999 |
| JP | 2000506398 A | 5/2000 |
| JP | 2001178717 A | 7/2001 |
| JP | 2003325518 A | 11/2003 |
| JP | 2004195228 A | 7/2004 |
| JP | 2004529697 A | 9/2004 |
| JP | 2005095376 A | 4/2005 |
| JP | 2006325746 A | 12/2006 |
| JP | 2007090075 A | 4/2007 |
| JP | 2007536048 A | 12/2007 |
| JP | 2008073338 A | 4/2008 |
| JP | 2009028194 A | 2/2009 |
| JP | 2009100971 A | 5/2009 |
| JP | 2010158360 A | 7/2010 |
| JP | 2011507647 A | 3/2011 |
| JP | 2011140527 | 7/2011 |
| JP | 2013503681 A | 2/2013 |
| JP | 2014161735 A | 9/2014 |
| JP | 2016025993 A | 2/2016 |
| WO | 9115244 | 10/1991 |
| WO | 9115244 A2 | 10/1991 |
| WO | 9115244 A3 | 10/1991 |
| WO | 9409829 A1 | 5/1994 |
| WO | 9516467 A1 | 6/1995 |
| WO | 9746159 A1 | 12/1997 |
| WO | 0101865 A1 | 1/2001 |
| WO | 2004110279 A1 | 12/2004 |
| WO | 2005116902 A2 | 12/2005 |
| WO | 2006015971 A1 | 2/2006 |
| WO | 2006018433 A1 | 2/2006 |
| WO | 2006067201 A2 | 6/2006 |
| WO | 2006090309 A2 | 8/2006 |
| WO | 2006108868 A1 | 10/2006 |
| WO | 2007054544 A1 | 5/2007 |
| WO | 2008136201 A1 | 11/2008 |
| WO | 2009083557 A1 | 7/2009 |
| WO | 2010058014 A1 | 5/2010 |
| WO | 2010142694 A1 | 12/2010 |
| WO | 2011026866 A1 | 3/2011 |
| WO | 2011110552 A1 | 9/2011 |
| WO | 2014096041 A1 | 6/2014 |

OTHER PUBLICATIONS

Frinking et al., "Subharmonic Scattering of Phospholipid-Shell Microbubbles at Low Acoustic Pressure Amplitudes", "IEEE Transactions on Ultrasonics, Ferroelectrics, and Frequency Control; Aug. 2010", , vol. 57, No. 8, Publisher: IEEE.

U.S. Patent and Trademark Office, "Office Action", U.S. Appl. No. 13/607,354, dated Aug. 31, 2015, pp. 1-11, Published: US.

U.S. Patent and Trademark Office, "Office Action", U.S. Appl. No. 13/607,354, dated Sep. 17, 2014, pp. 1-35, Published: US.

U.S. Patent and Trademark Office, "Office Action", U.S. Appl. No. 14/654,449, dated Dec. 2, 2016, pp. 1-18, Published: US.

U.S. Patent and Trademark Office, "Office Action", U.S. Appl. No. 15/781,088, dated Jan. 23, 2019, pp. 1-10, Published: US.

Wang et al., "Self-adaptive Contrast Enhancement Algorithm for Infrared Images based on Plateau Histogram", Acta Photonica Sinica, vol. 34, No. 2, Feb. 28, 2005, China Academic Journal Electronic Publishing House, Bejing, China, http://www.cnki.net, pp. 1-3.

Zhang, et al., "A Novel Model for Contrast Enhanced Ultrasound Video and Its Applications", IEEE Ultrasonics Symposium, 2006, pp. 1726-1729, IEEE.

Japanese Patent Office, "Office Action from JP Application No. 2016-561335 dated Nov. 2, 2018", from Foreign Counterpart to PCT Application No. PCT/EP2015/097020, Nov. 2, 2018, pp. 1-5, Published: JP (English language translation included).

Andreas et al., "Towards a Model-Free Denoising of Underwater Optical Images", Oceans-Europe 2005, vol. 1, Jun. 20, 2005, pp. 527-532.

Canadian Intellectual Property Office, "Office Action from CA Application No. 2769164 dated May 26, 2016", from Foreign Counterpart to PCT Application No. PCT/EP2010/062816, May 26, 2016, pp. 1-4, Published: CA.

European Patent Office, "Communication pursuant to Article 94(3) from EP Application No. 13814107.2 dated Apr. 20, 2016", from

(56) References Cited

OTHER PUBLICATIONS

Foreign Counterpart to PCT Application No. PCT/EP2013/077152, Apr. 20, 2016, pp. 1-5, Published: EP.
Fisher et al., "Contrast Stretching", Histogram Equalization, Internet Citation, 1994, XP002291289, retrieved from internet: http://www.cee.hw.ac.uk/hipr/html/stretch.html.
Futterer et al., "Prostate Cancer Localization with Dynamic Contrast-enhanced MR Imaging and Proton MR Spectroscopic Imaging", Radiology, Nov. 2006, pp. 1-11, vol. 241, No. 2, RSNA.
Greis, "Technology overview: SonoVue (Bracco, Milan)", European Radiology, Nov. 2004, pp. 1-6, Springer-Verlag 2004.
International Bureau, "International Preliminary Report on Patentability from PCT Application No. PCT/EP2008/068247 dated Jun. 29, 2010", from Foreign Counterpart to EP Application No. 07124133.5, Jun. 29, 2010, pp. 1-7, Published: Switzerland.
International Bureau, "International Preliminary Report on Patentability from PCT Application No. PCT/EP2011/053460 dated Sep. 11, 2012", from Foreign Counterpart to EP Application No. 10155926.8, Sep. 11, 2012, pp. 1-8, Published: Switzerland.
International Searching Authority, "International Search Report and Written Opinion from PCT Application No. PCT/EP2010/058031 dated Nov. 29, 2010", from Foreign Counterpart to EP Application No. 09162171.4, Nov. 29, 2010, pp. 1-5, Published: EP.
International Searching Authority, "International Search Report and Written Opinion from PCT Application No. PCT/EP2016/079836 dated Feb. 2, 2017", from Foreign Counterpart to EP Application No. 15199217.9, Feb. 2, 2017, pp. 1-16, Published: EP.
International Searching Authority, "International Search Report from PCT Application No. PCT/EP2008/068247 dated Apr. 20, 2009", from Foreign Counterpart to EP Application No. 07124133.5, Apr. 20, 2009, pp. 1-5, Published: WO.
International Searching Authority, "International Search Report from PCT Application No. PCT/EP2010/062816 dated Oct. 13, 2010", from Foreign Counterpart to EP Application No. 09169189.9, Oct. 13, 2010, pp. 1-4, Published: EP.
International Searching Authority, "International Search Report from PCT Application No. PCT/EP2011/053460 dated May 16, 2011", from Foreign Counterpart to EP Application No. 10155926.8, May 16, 2011, pp. 1-6, Published: WO.
International Searching Authority, "International Search Report from PCT Application No. PCT/EP2013/077152 dated Apr. 4, 2014", from Foreign Counterpart to EP Application No. 12199175.6, Apr. 4, 2014, pp. 1-5, Published: WO.
Japanese Patent Office, "Notification of Reasons for Refusal from JP Application No. 2012-514452 dated Jan. 7, 2014", from Foreign Counterpart to PCT Application No. PCT/EP2010/058031, Jan. 7, 2014, pp. 1-6, Published: JP.
Japanese Patent Office, "Office Action from JP Application No. 2010-540122 dated Nov. 26, 2014", from Foreign Counterpart to PCT Application No. PCT/EP2008/068247, Nov. 26, 2014, pp. 1-2, Published: JP.
Kim et al., "Wash-In Rate on the Basis of Dynamic Contrast-Enhanced MRI: Usefulness for Prostate Cancer Detection and Localization", Journal of Magnetic Resonance Imaging, 2005, pp. 1-8, Wiley-Liss, Inc.
Krix et al., "Quantification of Perfusion of Liver Tissue and Metastases Using a Multivessel Model for Replenishment Kinetics of Ultrasound Contrast Agents", Ultrasound in Medicine and Biology, 2004, pp. 1355-1363, vol. 30, No. 10, World Federation for Ultrasound in Medicine and Biology.
Lanza, et al., "Targeted Ultrasonic Contrast Agents for Molecular Imaging and Therapy", Progress in Cardiovascular Diseases, Jul./Aug. 2001, pp. 13-31, vol. 44, No. 1, W.B Saunders Company.
Lindner, et al., "Albumin Microbubble Persistence During Myocardial Contrast Echocardiography Is Associated With Microvascular Endothelial Glycocalyx Damage", Circulation Journal of the American Heart Association, 1998, pp. 1-9, American Heart Association.
Linton, et al., "A new method of analysing indicator dilution curves", Cardiovascular Research, Jan. 9, 1995, pp. 1-10, Elsevier Science B.V.
Mohs, et al., "An Integrated Widefield Imaging and Spectroscopy System for Contrast-Enhanced, Image-Guided Resection of Tumors", IEEE Transactions on Biomedical Engineering, vol. 62, No. 5, May 2015; pp. 1416-1424.
Pochon, et al., "BR55: A Lipopeptide-Based VEGFR2-Targeted Ultrasound Contrast Agent for Molecular Imaging of Angiogenesis", Investigative Radiology, Feb. 2010, pp. 1-7, vol. 45, No. 2, Lippincott Williams and Wilkins.
Po-Hsiang et al., "Imaging Local Scatterer Concentrations by the Nakagami Statistical Model", Ultrasound in Medicine and Biology, New Nork, NY, US, vol. 33, No. 4, Mar. 27, 2007, pp. 608-619.
Rafter, et al., "Imaging technologies and techniques", Cardiology Clinics, 2004, pp. 181-197, Elsevier Inc.
Rognin et al., "A New Method for Enhancing Dynamic Vascular Patterns of Focal Liver Lesions in Contrast Ultrasound", IEEE Ultrasonics Symposium, 2007, pp. 546-549, IEEE.
State Intellectual Property Office, P.R. China, "Office Action from CN Application No. 201080025290.5 dated Sep. 2, 2013", from Foreign Counterpart to PCT Application No. PCT/EP2010/058031, Sep. 2, 2013, pp. 1-24, Published: CN.
State Intellectual Property Office, P.R. China, "Office Action from CN Application No. 201380066958.4 dated Mar. 31, 2017", from Foreign Counterpart to PCT Application No. PCT/EP2013/077152, Mar. 31, 2017, pp. 1-23, Published: CN.
State Intellectual Property Office, P.R. China, "Office Action from CN Application No. 201580011243.8 dated Dec. 5, 2018", Dec. 5, 2018, pp. 1-34, Published: CN.
Tardy, et al., "Ultrasound Molecular Imaging of VEGFR2 in a Rat Prostate Tumor Model Using BR55", Investigative Radiology, Oct. 2010, pp. 573-578, vol. 45, No. 10, Lippincott Williams and Wilkins.
U.S. Patent and Trademark Office, "Advisory Action", U.S. Appl. No. 12/811,089, dated Jan. 15, 2015, pp. 1-3, Published: US.
U.S. Patent and Trademark Office, "Advisory Action", U.S. Appl. No. 12/811,089, dated Feb. 12, 2014, pp. 1-3, Published: US.
U.S. Patent and Trademark Office, "Advisory Action", U.S. Appl. No. 13/377,143, dated Oct. 21, 2014, pp. 1-6, Published: US.
U.S. Patent and Trademark Office, "Final Office Action", U.S. Appl. No. 12/811,089, dated Oct. 28, 2013, pp. 1-22, Published: US.
U.S. Patent and Trademark Office, "Final Office Action", U.S. Appl. No. 12/811,089, dated Sep. 17, 2014, pp. 1-10, Published: US.
U.S. Patent and Trademark Office, "Final Office Action", U.S. Appl. No. 13/377,143, dated Jul. 24, 2014, pp. 1-41, Published: US.
U.S. Patent and Trademark Office, "Final Office Action", U.S. Appl. No. 13/607,354, dated Sep. 2, 2016, pp. 1-11, Published: US.
U.S. Patent and Trademark Office, "Notice of Allowability", U.S. Appl. No. 14/654,449, dated May 18, 2017, pp. 1-6, Published: US.
U.S. Patent and Trademark Office, "Notice of Allowance", U.S. Appl. No. 12/811,089, dated Mar. 2, 2015, pp. 1-16, Published: US.
U.S. Patent and Trademark Office, "Notice of Allowance", U.S. Appl. No. 13/377,143, dated Dec. 7, 2015, pp. 1-11, Published: US.
U.S. Patent and Trademark Office, "Notice of Allowance", U.S. Appl. No. 13/393,633, dated Sep. 3, 2014, pp. 1-17, Published: US.
U.S. Patent and Trademark Office, "Notice of Allowance", U.S. Appl. No. 13/607,354, dated Jul. 12, 2018, pp. 1-9, Published: US.
U.S. Patent and Trademark Office, "Notice of Allowance", U.S. Appl. No. 14/654,449, dated Apr. 13, 2017, pp. 1-7, Published: US.
U.S. Patent and Trademark Office, "Office Action", U.S. Appl. No. 12/811,089, dated Mar. 28, 2013, pp. 1-27, Published: US.
U.S. Patent and Trademark Office, "Office Action", U.S. Appl. No. 12/811,089, dated Apr. 24, 2014, pp. 1-18, Published: US.
U.S. Patent and Trademark Office, "Office Action", U.S. Appl. No. 13/377,143, dated Jan. 8, 2014, pp. 1-41, Published: US.
U.S. Patent and Trademark Office, "Office Action", U.S. Appl. No. 13/377,143, dated Aug. 14, 2015, pp. 1-9, Published: US.
U.S. Patent and Trademark Office, "Office Action", U.S. Appl. No. 13/393,633, dated Apr. 7, 2014, pp. 1-10, Published: US.
U.S. Patent and Trademark Office, "Office Action", U.S. Appl. No. 13/607,354, dated Feb. 10, 2015, pp. 1-8, Published: US.
U.S. Patent and Trademark Office, "Office Action", U.S. Appl. No. 13/607,354, dated Jul. 5, 2017, pp. 1-7, Published: US.

(56) References Cited

OTHER PUBLICATIONS

China National Intellectual Property Administration, "Second Office Action from CN Application No. 2015800112418 dated Apr. 25, 2019", pp. 111, Published: CN.

* cited by examiner

ESTIMATION OF ACOUSTIC LEVEL IN-SITU WITH NON-FUNDAMENTAL ANALYSIS

TECHNICAL FIELD

The solution according to the present disclosure relates to the field of medical applications. More specifically, this solution relates to the use of ultrasound scanners.

BACKGROUND

Ultrasound scanners are routinely used in a number of medical applications. A typical example is in diagnostic applications. In this case, ultrasound waves are applied to a body-part of a patient to be analyzed; corresponding echo signals that are recorded in response thereto may be used to create anatomical images (providing a morphological representation of the body-part) or parametric images (providing a spatial distribution of characteristic parameters of the body-part). More recently, the ultrasound scanners have also been introduced in therapeutic applications. In this case, the ultrasound waves are applied to the body-part so as to induce biological effects thereon deliberately; particularly, it is possible to obtain reversible cellular effects (for example, by acoustic (micro) streaming), or cellular death (for example, by indirect effects of (inertial) acoustic cavitation). Typical examples of these therapeutic applications are sonoporation, sonothrombolysis and high intensity focused ultrasound (HIFU) therapy.

The ultrasound scanners may also involve the use of an (ultrasound) contrast agent (UCA), for example, made of a suspension of phospholipid-stabilized gas-filled microbubbles. Particularly, in the diagnostic applications, the reflective characteristics of particles (for example, microbubbles) of the contrast agent facilitate its tracking (for example, to obtain blood perfusion information since the contrast agent flows at the same velocity as red-blood cells in the patient). Moreover, in the therapeutic applications, the contrast agent particles may act as micro-streaming promoters or cavitation nuclei.

A level of acoustic pressure applied to the contrast agent particles by the ultrasound waves largely varies according to the different medical applications. For example, in the diagnostic applications the acoustic pressure should be relatively low to avoid any undesired biological effect on the body-part that might be induced by thermal or non-thermal mechanisms. Conversely, relatively high acoustic pressures are required in the therapeutic applications to achieve the desired effects. For example, acoustic streaming is known to exist when the contrast agent particles oscillate in a stable and reversible way, whereas, in conditions of acoustic cavitation, the contrast agent particles oscillate more violently, eventually leading to their destruction.

The determination of the acoustic pressure that is actually applied in-situ to the contrast agent is relatively simple in in-vitro conditions (wherein it may be measured directly). However, this is very difficult (or even impossible) in in-vivo conditions. Indeed, in this case the acoustic pressure may not be measured in the body-part and it may normally only be estimated from the acoustic pressure of the ultrasound waves that are provided by the ultrasound scanner. However, anatomical structures of the patient interposed between a transducer of the ultrasound scanner and the body-part strongly interfere with the transmission of the ultrasound waves. As a result, the ultrasound waves are subject to attenuation, with a progressive reduction of their acoustic pressure, and thus of energy, during propagation through the anatomical structures. The main source of attenuation of the ultrasound waves (in addition to a minor reflection/scattering thereof) is their absorption by the anatomical structures, wherein the energy of the ultrasound waves is converted to heat (and it is then lost). Moreover, the presence of the contrast agent may also dramatically affect the attenuation of the ultrasound waves. Particularly (in addition to attenuating the energy of the ultrasound waves linearly according to its concentration), the contrast agent has non-linear characteristics that involve a strong dependence of the attenuation of the ultrasound waves on their energy and frequency.

As a consequence, it is not possible to accurately control the acoustic pressure that is actually applied in-situ to the contrast agent particles or to their surroundings. This may hinder several medical applications of the ultrasound scanners in practice. Particularly, the difficulty of controlling the acoustic pressure is detrimental to several therapeutic applications (for example, when a stable and reversible oscillation of the contrast agent particles is required, such as in sonothrombolysis); indeed, since the acoustic pressure that is applied to the contrast agent particles determines their oscillation, the lack of an accurate knowledge thereof may reduce the efficiency of the therapeutic applications (when too low) or it may cause undesired side effects due to an overexposure to the ultrasound waves (when too high).

SUMMARY

A simplified summary of the present disclosure is herein presented in order to provide a basic understanding thereof; however, the sole purpose of this summary is to introduce some concepts of the disclosure in a simplified form as a prelude to its following more detailed description, and it is not to be interpreted as an identification of its key elements nor as a delineation of its scope.

In general terms, the present disclosure is based on the idea of exploiting non-fundamental echo responses.

More specifically, an aspect provides a method for use with an ultrasound scanner, wherein an estimate value (particularly, a power level of the ultrasound scanner that is required to apply a desired acoustic pressure level to the body-part, the acoustic pressure level that is actually applied to the body-part when a specific power level is set, an acoustic attenuation that occurs within a patient between a transducer of the ultrasound scanner and the body-part and/or the acoustic attenuation that occurs within the patient between different body-parts) is determined according to a comparison between measurement data (based on a measurement response comprising a non-fundamental component of a measurement echo signal received in response to a measurement excitation signal) and corresponding reference data.

A further aspect provides a corresponding computer program.

A further aspect provides a corresponding computer program product.

A further aspect provides a corresponding system.

A further aspect provides a corresponding therapeutic method.

A further aspect provides a corresponding diagnostic method.

Still more specifically, one or more aspects of the present disclosure are set out in the independent claims and advantageous features thereof are set out in the dependent claims, with the wording of all the claims that is herein incorporated verbatim by reference (with any advantageous feature provided with reference to a specific aspect that applies mutatis mutandis to every other aspect).

BRIEF DESCRIPTION OF THE DRAWINGS

The solution of the present disclosure, as well as further features and the advantages thereof, will be best understood with reference to the following detailed description, given purely by way of a non-restrictive indication, to be read in conjunction with the accompanying drawings (wherein, for the sake of simplicity, corresponding elements are denoted with equal or similar references and their explanation is not repeated, and the name of each entity is generally used to denote both its type and its attributes—such as value, content and representation). Particularly.

DETAILED DESCRIPTION

Figure 1:
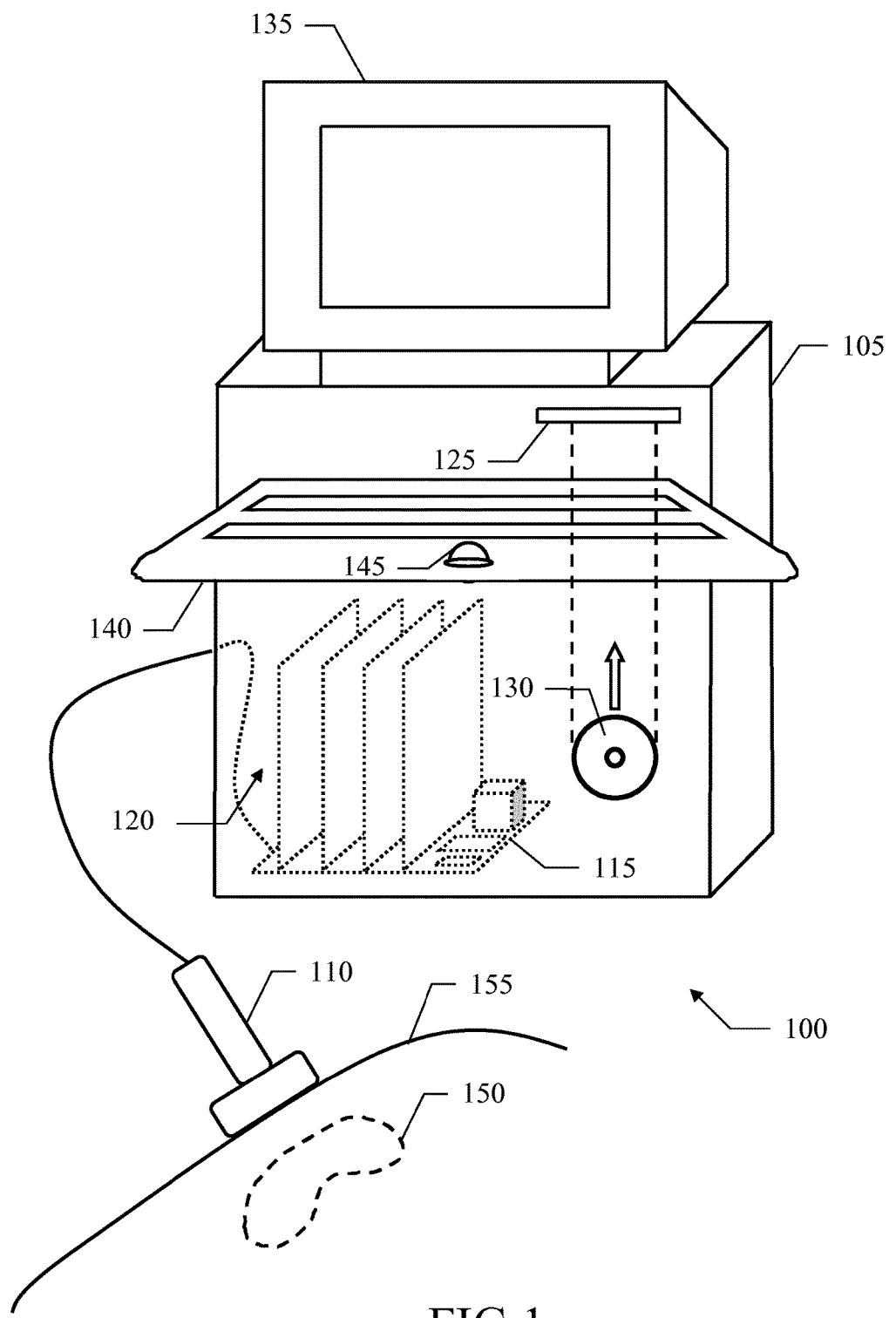
FIG. 1 shows a pictorial representation of an ultrasound scanner that may be used to practice the solution according to an embodiment of the present disclosure.

With reference in particular to the FIG. 1, a pictorial representation is shown of an ultrasound scanner 100 that may be used to practice the solution according to an embodiment of the present disclosure.

The ultrasound scanner 100 comprises a central unit 105 and a hand-held transmit-receive imaging probe, or transducer, 110 of the array type connected thereto. The transducer 110 comprises a transmitter for transmitting a succession of ultrasound waves intended to generate frames of anatomical images (for example, with a rate of 4-20 Hz), and a receiver for receiving (radio-frequency, RF) echo signals resulting from the reflection of the ultrasound waves in a selected scan plane; for this purpose, the transducer 110 is provided with a transmit/receive multiplexer, which allows using the transducer 110 in the above-described pulse-echo mode.

The central unit 105 houses a motherboard 115, on which electronic circuits controlling operation of the ultrasound scanner 100 are mounted (for example, a microprocessor, a working memory and a hard disk drive). Moreover, one or more daughter boards (denoted as a whole with the reference 120) are plugged in the motherboard 115; the daughter boards 120 provide further electronic circuits for driving the transducer 110 and for processing the echo signals. The central unit 105 is also equipped with a drive 125 for reading/writing removable disks 130 (such as CDs or DVDs). A monitor 135 is connected to the central unit 105 for displaying information relating to a therapeutic/diagnostic process that is in progress.

Operation of the ultrasound scanner 100 is controlled by means of a keyboard 140 (connected to the central unit 105 in a conventional manner); preferably, the keyboard 140 is provided with a trackball 145 that is used to manipulate the position of a pointer (not shown in the figure) on the monitor 135. Particularly, the keyboard 140 allows setting a desired (center) frequency of the ultrasound waves within an allowed frequency range (for example, from 1 and 50 MHz), and a desired transmission power of the ultrasound system generating the ultrasound waves within an allowed range (for example, corresponding to an amplitude thereof defined by a transmission voltage from 1 mV to 10 V). In most ultrasound scanners, it is not possible to set the transmission power in absolute terms, but only in relative terms as a dimensionless power level thereof; for example, the power level is expressed in dB with respect to a reference value, such as a maximum value (for example, from −40 dB to 0 dB).

The ultrasound scanner 100 may be used in therapeutic applications and in diagnostic applications to treat and to analyze, respectively, a body-part 150 of a patient 155. For this purpose, an (ultrasound) contrast agent is generally administered to the patient 155.

The contrast agent comprises particles acting as ultrasound reflectors. For example, the contrast agent is a suspension of gas-filled bubbles in a liquid carrier; typically, the gas-filled bubbles have diameters approximately 0.1-5 µm, so as to allow their retaining within the vascular system of the patient 155, but at the same time to allow their passage through capillaries. The gas-filled bubbles are generally stabilized by entraining or encapsulating the gas or a precursor thereof into a variety of systems, comprising phospholipids, emulsifiers, oils, thickeners, sugars, proteins or polymers; stabilized gas-filled bubbles are generally referred to as microvesicles. Particularly, microvesicles dispersed in an aqueous medium and bounded at the gas/liquid interface by a very thin envelope involving a surfactant (i.e., an amphiphilic material) are also known as microbubbles. Alternatively, microvesicles surrounded by a solid material envelope formed by lipids or (natural or synthetic) polymers, are also known as microballoons or microcapsules. Another kind of contrast agent comprises a suspension of porous microparticles of polymers or other solids, which carry bubbles of gas entrapped within the pores of the microparticles, or adsorbed on their surfaces. Examples of suitable aqueous suspensions of microvesicles, in particular microbubbles and microballoons, and of the preparation thereof are described in EP-A-0458745, WO-A-91/15244, EP-A-0554213, WO-A-94/09829 and WO-A-95/16467 (the entire disclosures of which are herein incorporated by reference). An example of a commercial contrast agent comprising microvesicles is SonoVue by Bracco International BV (trademarks).

For example, the contrast agent is administered to the patient 155 intravenously as a bolus—i.e., a single dose provided by hand with a syringe over a short period of time (of the order of 2-20 seconds). The contrast agent circulates within the vascular system of the patient 155, so as to perfuse the body-part 150. At the same time, the transducer 110 is placed in contact with the skin of the patient 155 in the area of the body-part 150, and a sequence of ultrasound waves is applied thereto. In the therapeutic applications, the ultrasound waves deliberately induce biological effects on the body-part 150 (for example, acoustic streaming or acoustic cavitation). In the diagnostic applications, instead, the echo signals that are recorded in response to the ultrasound waves provide a representation of the body-part 150.

In the solution according to an embodiment of the present disclosure (as described in detail in the following), an estimate value is determined; the estimate value indicates the power level that is required to apply a desired acoustic pressure to the body-part 150, the acoustic pressure that is actually applied to the body-part 150 when a specific target power level is set, an acoustic attenuation that occurs within the patient 155 between the transducer 110 and the body-part 150 and/or the acoustic attenuation that occurs within the patient between different body-parts 150 (for example, at different depths). For this purpose, a non-fundamental (for example, a sub-harmonic) response of the contrast agent particles to the ultrasound waves is exploited; indeed, the typical patterns present in this non-fundamental response provide valuable information for the above-mentioned estimations.

Figure 2:
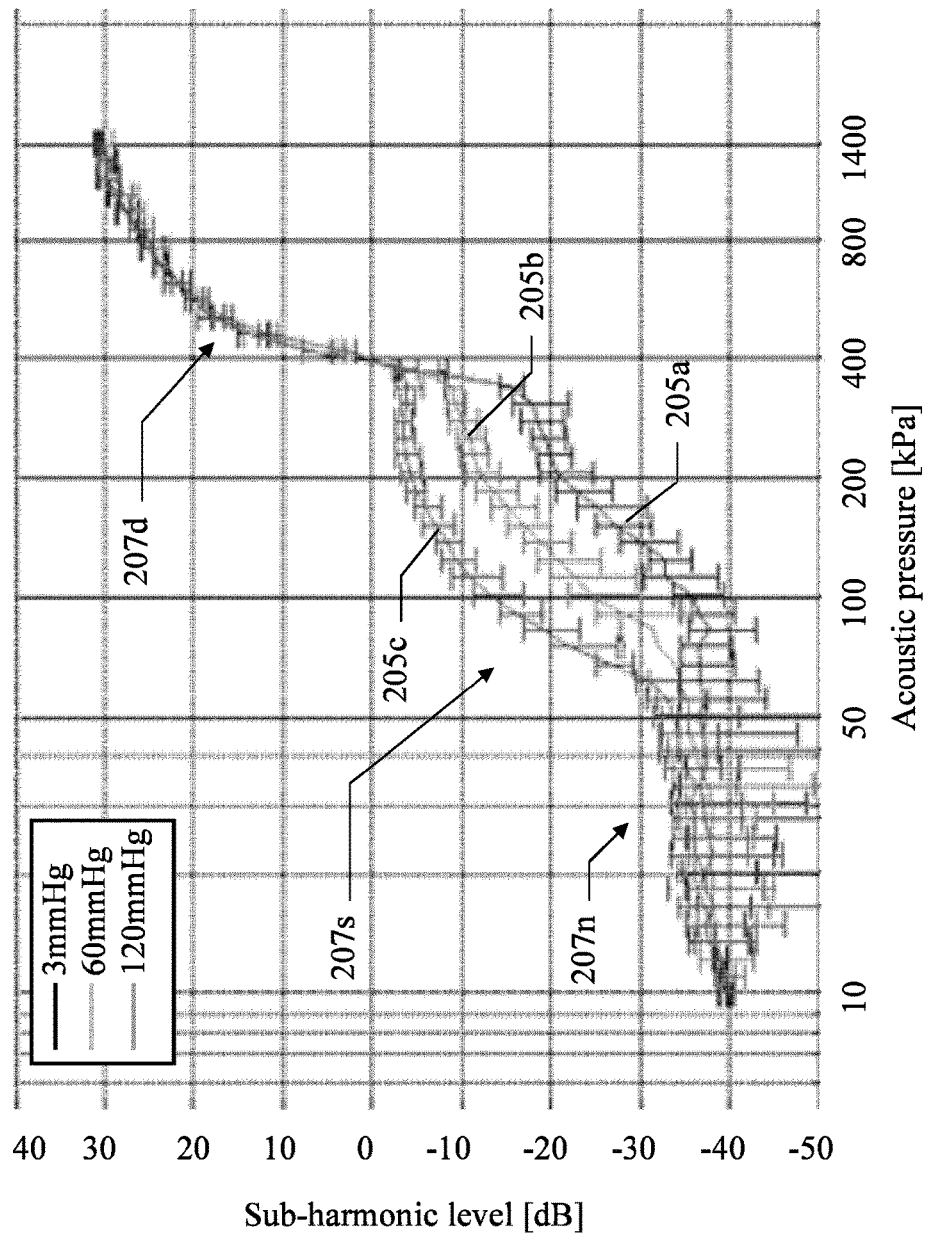
FIG. 2 shows different examples of sub-harmonic responses from contrast agent particles to ultrasound waves.

With reference now to the FIG. 2, different examples are shown of sub-harmonic responses from contrast agent particles to ultrasound waves.

Generally, the sub-harmonic response is defined by a level of a sub-harmonic component of the echo signal (for example, the power of the component having a frequency equal to one half (½) a fundamental/transmit frequency of the ultrasound waves) as a function of the acoustic pressure that is applied to the contrast agent particles by the ultrasound waves The sub-harmonic response may be represented, in a diagram plotting the sub-harmonic level (in dB with respect to a reference value) on the ordinate axis against the acoustic pressure (in kPa on a logarithmic scale) on the abscissa axis, with a corresponding sequence of points each one indicating the sub-harmonic level that is recorded when the corresponding acoustic pressure is applied to the contrast agent.

Particularly, the figure shows three sub-harmonic responses 205a, 205b and 205c. Each point of the sub-harmonic responses 205a-205c represents an average of the sub-harmonic levels that have been recorded for the corresponding acoustic pressure (with an error bar indicating their standard deviation); particularly, the sub-harmonic responses 205a, 205b and 205c relate to measures performed at different (ambient) hydrostatic pressures, and particularly at 3 mmHg, 60 mmHg and 120 mmHg, respectively.

The sub-harmonic responses 205a-205c comprise an initial portion, referred to as noise portion 207n (for example, below 50 kPa), which is not significant because of a predominant effect of a measurement noise. Considering instead higher acoustic pressures, as it is known the sub-harmonic level strongly depends on the hydrostatic pressure; this is confirmed by the differences among a central portion of the sub-harmonic responses 205a-205c, referred to as sensitive portion 207s (for example, from 50 kPa to 350 kPa). For example, the dependence of the sub-harmonic level from the hydrostatic pressure may be exploited for non-invasive hydrostatic pressure measurements in heart cavities or big vessels in the human body, as mentioned in Frinking PJA et al., "Subharmonic scattering of phospholipid-shell microbubbles at low acoustic pressure amplitude", IEEE Trans. Ultrason. Ferroelectr. Freq. Control, Vol. 57, No 8, August 2010 (the entire disclosure of which is herein incorporated by reference). Surprisingly, however, it has been found that the sub-harmonic level is substantially insensitive to the hydrostatic pressure for acoustic pressures higher than a transition acoustic pressure (for example, about 300-400 kPa); this is shown in the figure by the good overlap of a final portion of the sub-harmonic responses 205a-205c, referred to as destructive portion 207d (above this transition acoustic pressure, such as 350 kPa).

Moreover, according to theory the sub-harmonic response depends on an acoustic attenuation (for example, expressed in dB), both in the transmission of the ultrasound waves and in the receiving of the corresponding echo signals. Indeed, in a transmission path the acoustic attenuation (from the transducer of the ultrasound scanner to the depth of interest) reduces the acoustic pressure that is applied to the contrast agent; on a receiving path, instead, the acoustic attenuation (from the depth of interest to the transducer of the ultrasound scanner) reduces the sub-harmonic level that is recorded. Likewise, the contrast agent may also act as an acoustic attenuator that causes an acoustic attenuation proportional to its concentration when present along a propagation (i.e., transmission and/or receiving) path.

When the acoustic pressure is expressed on a logarithmic scale in the abscissa axis, the destructive portion of any sub-harmonic response has a constant pattern (irrespectively of the hydrostatic pressure, the acoustic attenuation and the contrast agent concentration), with the acoustic attenuation and the contrast agent concentration that only cause a shift thereof: a horizontal shift to reflect attenuation on the transmit path, and a vertical shift to reflect attenuation on the receive path.

Similar considerations apply when the sub-harmonic response is expressed by the sub-harmonic level as a function of the power level of the ultrasound scanner. In this case, the sub-harmonic response may be expressed, in a diagram (not shown in the figure) plotting the sub-harmonic level on the ordinate axis against the power level on the abscissa axis (both of them in dB), with a corresponding sequence of points each one indicating the sub-harmonic level that is recorded when the ultrasound scanner is set to the corresponding power level. As above, the sub-harmonic responses for different hydrostatic pressures comprise a noise portion that is not significant, a central portion that strongly depends on the hydrostatic pressure and a destructive portion that is substantially insensitive to the hydrostatic pressure; the destructive portion of any sub-harmonic response has a constant pattern (irrespectively of the hydrostatic pressure, the acoustic attenuation and the contrast agent concentration), with the acoustic attenuation and the contrast agent concentration that only cause a (horizontal and vertical) shift thereof.

As a consequence, a comparison may be made between a measurement (sub-harmonic) response and a reference (sub-harmonic) response. Particularly, as described in detail in the following, the measurement response expresses the sub-harmonic level of a (measurement) echo signal that is measured as a function of the power level of the ultrasound scanner that is used to apply the ultrasound waves to the body-part (in-vivo), whereas the reference response expresses the sub-harmonic level of a (reference) echo signal that is provided as a function of the acoustic pressure or of the power level; for example, the reference response may be a calibration response that expresses the sub-harmonic level of a (calibration) echo signal that is measured as a function of the acoustic pressure and/or of the power level in an in-vitro calibration structure comprising the contrast agent, or it may be a further measurement response that expresses the sub-harmonic level of a further (measurement) echo signal (for example, measured at a different depth).

With reference now to the FIG. 3-FIG. 6, an example is shown of application of the solution according to an embodiment of the present disclosure.

Figure 3:
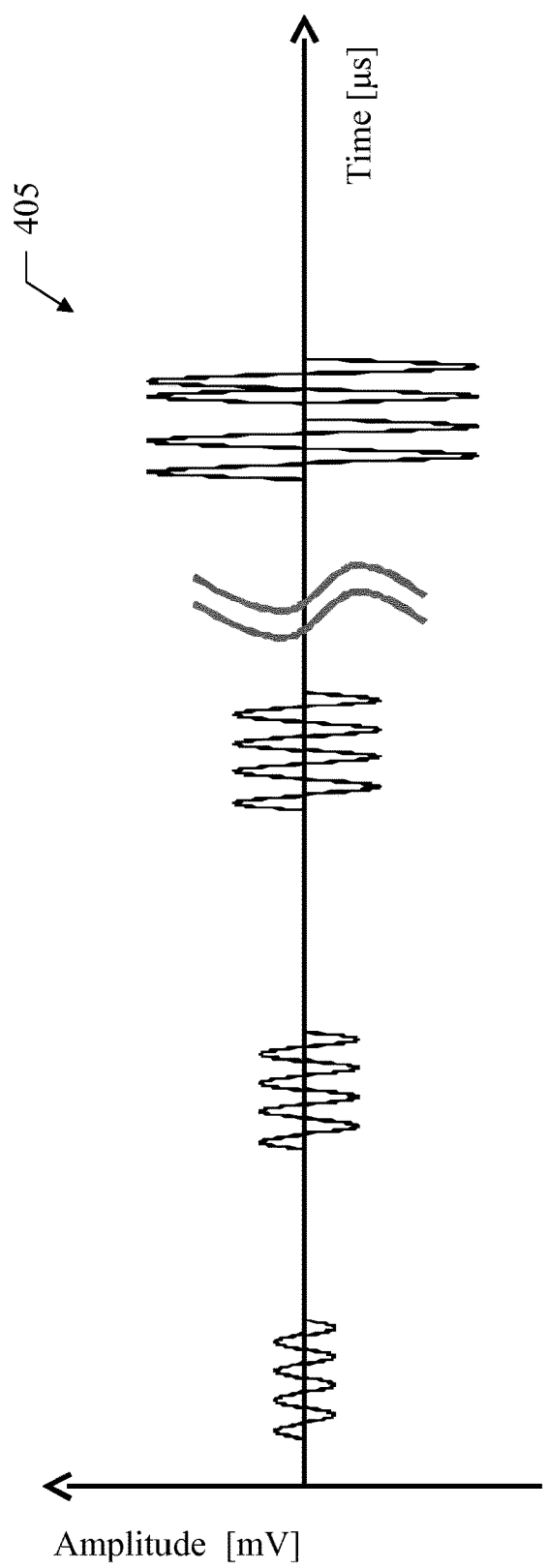
FIG. 3-FIG. 6 show an example of application of the solution according to an embodiment of the present disclosure.

Starting from the FIG. 3, the ultrasound waves that may be used to record the calibration/measurement response are defined by a calibration/measurement excitation signal 405, which is represented in the figure by plotting its amplitude on the ordinate axis (in mV) against the time on the abscissa axis (in µs). The calibration/measurement excitation signal 405 comprises a sequence of tone burst pulses with a relatively narrow band (for example, with a frequency of 1-10 MHz, and preferably 2-6 MHz); the amplitude of the resulting ultrasound pulses is modulated by varying the power level of the ultrasound scanner over time in a calibration/measurement range (for example, over 20 dB, and preferably over 30 dB).

In order to determine the calibration response, the calibration excitation signal 405 is applied in-vitro to the calibration structure (not shown in the figure). The calibration structure is a suspension of the contrast agent (for example, in water); the contrast agent has a relatively low concentration, avoiding any substantial acoustic attenuation (for example, lower than 5 dB/cm, and preferably lower than 2 dB/cm). For each ultrasound pulse of the calibration excitation signal 405 (as defined by the corresponding power level of the ultrasound scanner), the sub-harmonic level of the calibration echo signal received in response thereto and the actual acoustic pressure applied to the contrast agent (for example, measured with a hydrophone) are recorded. On the other hand, in order to determine the measurement response, the measurement excitation signal 405 is applied in-vivo to the body-part (perfused with the contrast agent); for each ultrasound pulse of the measurement excitation signal 405 (as defined by the corresponding power level of the ultrasound scanner), the sub-harmonic level of the measurement echo signal received in response thereto is recorded.

Figure 4:
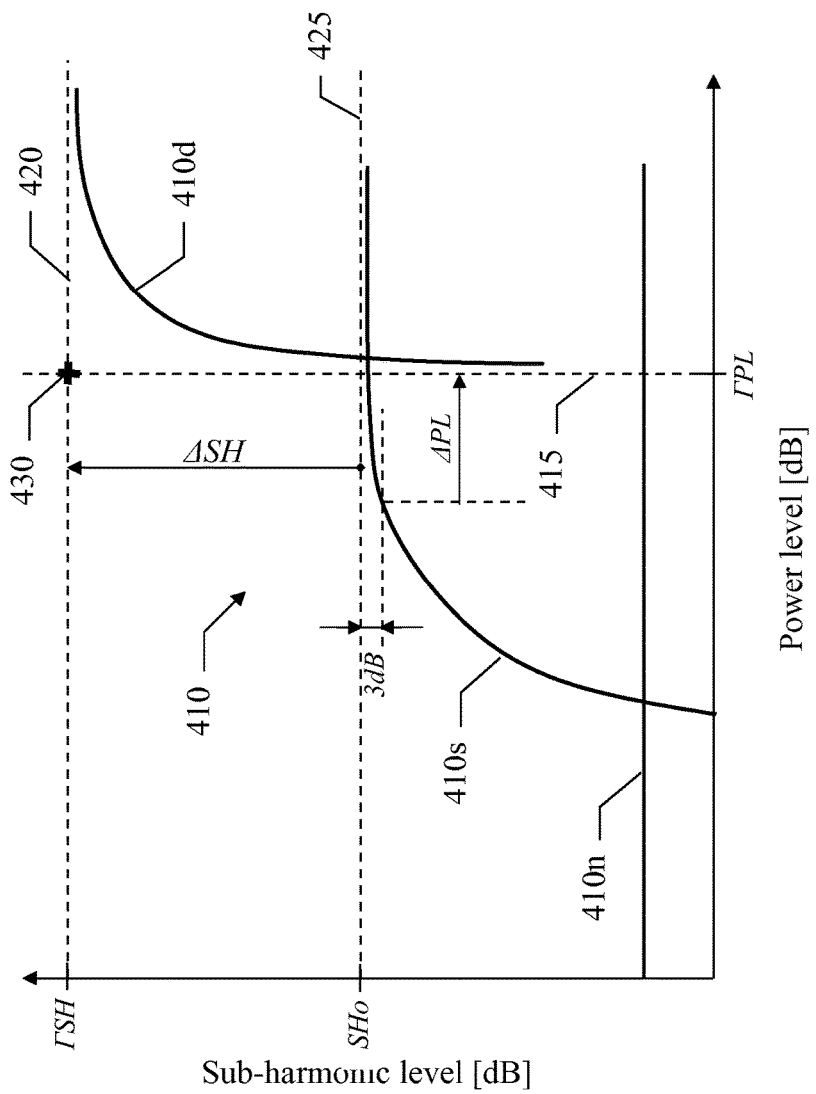

Moving to the FIG. 4, in an embodiment of the present disclosure the comparison of the measurement data with the reference data is based on corresponding instances of a same model function fitting the measurement response and the reference response (referred to as measurement function and reference function, respectively, with the reference function that may be a calibration function when fitting the calibration response or a further measurement function when fitting the further measurement response). Generally, the model function expresses the sub-harmonic level as a function of the power level or of the acoustic pressure on a logarithmic scale (for example, in dB). With reference in particular to the power level, the model function is represented (in a diagram plotting the sub-harmonic level on the ordinate axis against the power level on the abscissa axis, both of them expressed in dB) with a corresponding curve 410. The model function (i.e., its curve 410) comprises a noise segment 410*n* representing the noise portion, a sensitive segment 410*s* representing the sensitive portion, and a destructive segment 410*d* representing the destructive portion of the corresponding sub-harmonic response. The model function may have a generic S-shape. Particularly, the model function comprises an (initial) first constant segment having a substantially constant first value (defining the noise segment 410*n*). The model function then comprises a second constant segment with a substantially constant second value higher than the first value, and a first increasing segment between the first constant segment and the second constant segment substantially increasing monotonically, with a concave shape (defining the sensitive segment 410*s*). At the end, the model function comprises a (final) third constant segment with a substantially constant third value higher than the second value, and a second increasing segment between the second constant segment and the third constant segment substantially increasing monotonically, with a concave shape (defining the destructive segment 410*d*). More formally, the model function has the first derivative substantially equal to zero in the first/second/third constant segments, and it has the first derivative substantially higher than (or equal to) zero in the first/second increasing segments (with the model function that may also have the second derivative that is negative in the first/second increasing segments).

For example, the model function may be defined by the following expression:

$$SH(PL) = 10 \cdot \log \left( 10^{\left(\frac{\Gamma SH}{10}\right)} \cdot e^{\left(\frac{-10^{\left(\frac{Kd}{10}\right)} \cdot 10^{\left(\frac{\Gamma PL}{20}\right)}}{PL - 10^{\left(\frac{\Gamma PL}{20}\right)}}\right)} + \frac{e^{10^{\left(\frac{Ks}{20}\right)}} \cdot 10^{\left(\frac{\Gamma SH - \Delta SH}{10}\right)}}{e^{10^{\left(\frac{Ks}{20}\right)}} + e^{\left(\frac{10^{\left(\frac{Ks}{20}\right)} \cdot 10^{\left(\frac{\Gamma PL - \Delta PL}{20}\right)}}{PL}\right)}} + 10^{\left(\frac{Kn}{10}\right)} \right).$$

Particularly, the model function SH(PL) has an independent variable PL that represents the power level and a dependent variable SH that represents the sub-harmonic level (both of them in dB). The model function SH(PL) is composed of the sum of three terms defining its noise segment 410*n*, sensitive segment 410*s* and destructive segment 410*d*. In the first term (representing the destructive segment 410*d*), the parameter Kd is a form factor (in dB), the parameter ΓPL is the power level of a (descending) vertical asymptote 415 of the destructive segment 410*d* and the parameter ΓSH is the sub-harmonic level of an (increasing) horizontal asymptote 420 of the destructive segment 410*d* (i.e., with $$\lim_{PL \to \Gamma PL} SH(PL) = -\infty$$

and $$\lim_{PL \to +\infty} SH(PL) = \Gamma SH,$$

respectively). In the second term (representing the sensitive segment 410*s*), the parameter Ks is a form factor (in dB), the parameter ΔPL is the difference between the parameter ΓPL and the power level at which the sub-harmonic level is 3 dB below an (increasing) horizontal asymptote 425 of the sensitive segment 410*s* (i.e., with $$\lim_{PL \to +\infty} SH(PL) = SHo \Big),$$

and the parameter ΔSH is the difference between the power level of the horizontal asymptote 420 (i.e., the parameter ΓSH) and the power level of the horizontal asymptote 425 (i.e., SHo). In the third term (representing the noise segment 410*n*), the parameter Kn indicates the measurement noise (in dB). Each measurement/reference function is then defined by corresponding values of the parameters Kd, ΓPL, ΓSH, Ks, ΔPL, ΔSH and Kn that make the model function SH(PL) best fitting the measurement/reference response.

Similar considerations apply to the model function that expresses the sub-harmonic level as a function of the acoustic pressure; in this case, a model function SH(AP) may be defined as above, with an independent variable AP that represents the acoustic pressure, a parameter ΓAP for the acoustic pressure of the vertical asymptote of the destructive segment, and a parameter ΔAP for the difference between the parameter ΓAP and the acoustic pressure at which the sub-harmonic level is 3 dB below the horizontal asymptote of the sensitive segment.

In view of the above, the destructive segment of any measurement/reference function (corresponding to the destructive segment 410d of the model function) has a constant shape (irrespectively of the hydrostatic pressure, the acoustic attenuation and the contrast agent concentration); the destructive segment only shifts (substantially rigidly) according to the corresponding acoustic attenuation and contrast agent concentration. Therefore, in an embodiment of the present disclosure the comparison of the measurement function with the reference function is simply based on characteristic points of the destructive segments thereof (referred to as measurement point and reference point for the measurement function and for the reference function, respectively, with the reference point that may be a calibration point for the calibration function or a further measurement point for the further measurement function). Each measurement/reference point univocally identifies a position of the destructive segment of the corresponding measurement/reference function. For example, with reference in general to the curve 410 of the model function SH(PL), the characteristic point may be defined in correspondence to an intersection between the sensitive segment 410s and the destructive segment 410d. Particularly, the characteristic point may be defined by the intersection of the vertical asymptote 415 with the horizontal asymptote 420 of the destructive segment 410d (denoted with a cross 430 in the figure); the characteristic point then has the coordinates (ΓPL,ΓSH), with the parameter ΓPL that defines a characteristic power level (similar considerations apply when the characteristic point has the coordinates (ΓAP,ΓSH), with the parameter ΓAP that defines a characteristic acoustic pressure).

Figure 5:
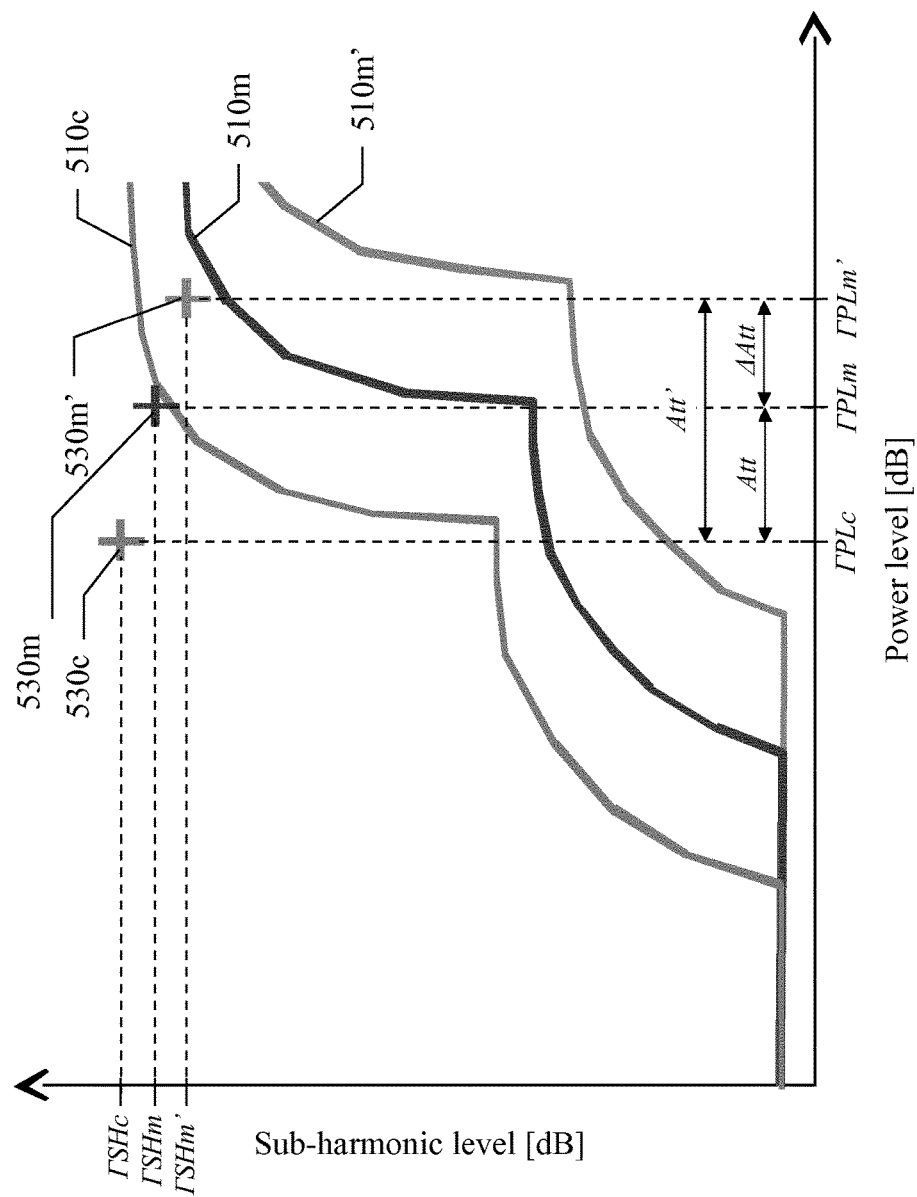

Moving to the FIG. 5, an exemplary calibration response (not shown in the figure) is fitted by a calibration function (denoted with SHc(PL)), which is represented by a (calibration) curve 510c. An exemplary measurement response (not shown in the figure) is instead fitted by a measurement function (denoted with SHm(PL)), which is represented by a (measurement) curve 510m. Generally, the measurement response is attenuated with respect to the calibration response (because of an attenuation in the patient caused by the anatomical structures interposed between the transducer of the ultrasound scanner and the body-part and/or because of the possibly relatively high concentration of the contrast agent). Therefore, the curve 510m is shifted rightwards with respect to the curve 510c (since higher power levels are now required to obtain the same sub-harmonic levels because of the acoustic attenuation in the transmission path) and downwards (since lower sub-harmonic levels are obtained from the same power levels because of the acoustic attenuation in the receiving path).

The calibration function SHc(PL) has the calibration point (ΓPLc,ΓSHc) that is represented by a (calibration) cross 530c. The calibration point (ΓPLc,ΓSHc) identifies the characteristic power level ΓPLc (referred to as calibration power level), which causes the application of the corresponding characteristic acoustic pressure ΓAPc to the contrast agent (referred to as calibration acoustic pressure), as measured in the calibration structure. The measurement function SHm (PL) has the measurement point (ΓPLm,ΓSHm) that is represented by a (measurement) cross 530m. The measurement point (ΓPLm,ΓSHm) identifies the characteristic power level ΓPLm (referred to as measurement power level), which is required to apply the same calibration acoustic pressure ΓPAc to the body-part, and which is higher than the calibration power level ΓPLc because of the acoustic attenuation occurring in the patient (equal to Att=ΓPLm−ΓPLc, when expressed in dB).

Another exemplary measurement response (not shown in the figure) is fitted by a measurement function (denoted with SHm′(PL)), which is represented by a (measurement) curve 510m′. This measurement response is more attenuated with respect to the previous measurement response (for example, because more anatomical structures are interposed and/or the contrast agent has a higher concentration), so that the curve 510m′ is shifted further rightwards and downwards than the curve 510m is (with respect to the curve 510c). The measurement function SHm′(PL) has the measurement point (ΓPLm′,ΓSHm′), represented by a (measurement) cross 530m′, which identifies the measurement power level ΓPLm′. In this case, a higher measurement power level ΓPLm′ is required to apply the same calibration acoustic pressure ΓPAc to the body-part because of the higher acoustic attenuation in the patient (equal to Att′=ΓPLm′−ΓPLc, with an increase of ΔAtt=ΓPLm′−ΓPLm with respect to the attenuation Att, when expressed in dB).

Figure 6:
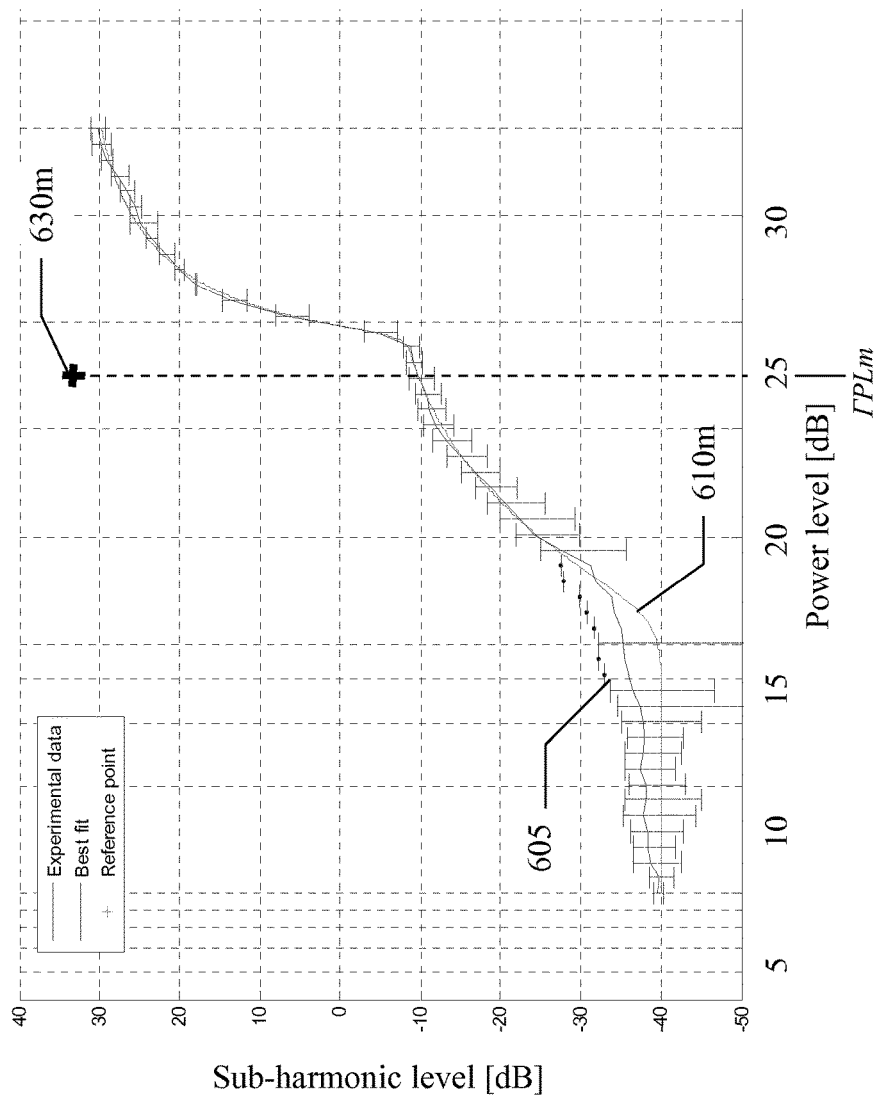

Moving to the FIG. 6, during an initialization phase of the ultrasound scanner the relevant calibration power level ΓPLc and calibration acoustic pressure ΓAPc may be determined (for example, ΓPLc=23 dB and ΓAPc=200 kPa); this operation is required only once for a specific environmental condition (for example, setting of the ultrasound scanner and type of the contrast agent).

A measurement response 605 is recorded from the body-part (perfused with the contrast agent). The measurement response 605 is fitted by a measurement function that is represented by a corresponding (measurement) curve 610m. The measurement function has the measurement point represented by a (measurement) cross 630m, which identifies the corresponding measurement power level ΓPLm (for example, ΓPLm=25 dB).

The measurement power level ΓPLm and the calibration acoustic pressure ΓAPc (in combination with the known quadratic relation between the acoustic pressure and the power of the ultrasound waves that are applied to the contrast agent, and with the known relation between the transmission power and the power level of the ultrasound scanner, in dB in the example at issue) may be used to estimate the acoustic pressure that is actually applied to the body-part for any power level of the ultrasound scanner or, vice-versa, the power level of the ultrasound scanner that is required to actually apply any acoustic pressure to the body-part. Particularly, when a target acoustic pressure APt is to be applied to the body-part, the ultrasound scanner is set to a target power level PLt given by:

$$PLt = \Gamma PLm + 20 \cdot \log\left(\frac{APt}{\Gamma APc}\right).$$

For example, in this case a target acoustic pressure APt=250 kPa may be applied to the body-part by setting the ultrasound scanner to a target power level $$PLt = 25 + 20 \cdot \log\left(\frac{250}{200}\right) = 26.94 \text{ dB}.$$

The above-described technique according to an embodiment of the present disclosure allows determining the actual acoustic pressure that is applied in-situ with a high accuracy; this result may be achieved even in in-vivo conditions, in a non-invasive and remote way.

The estimate of the acoustic pressure applied to the body-part so obtained may be used in therapeutic applications to control the ultrasound scanner so as to apply any desired acoustic pressure to the contrast agent particles. Particularly, when a stable and reversible oscillation of the contrast agent particles is required (for example, in sonothrombolysis), this significantly increases the efficiency of the therapeutic applications (for example, the cell lysis) at the same time avoiding, or at least substantially limiting, any undesired side effects due to overexposure to the ultrasound waves.

The measurement power level ΓPLm and the calibration power level ΓPLc may instead be used to estimate the acoustic attenuation occurring within the patient from the transducer to the body-part (hereinafter, referred to as total acoustic attenuation). Particularly, the total acoustic attenuation Att is simply given by the difference between the measurement power level ΓPLm and the calibration power level ΓPLc (i.e., Att=ΓPLm−ΓPLc). For example, in this case the total acoustic attenuation is equal to Att=25−23=2 dB.

In addition or in alternative, it is also possible to record a further measurement response from a further body-part still perfused with the contrast agent (for example, at a different depth of the same organ), and to fit it by a further measurement function having a further measurement point (not shown in the figure) that identifies a further measurement power level ΓPLm' (for example, ΓPLm'=25.3 dB at a point 1 cm deeper in the patient).

These two measurement power levels ΓPLm and ΓPLm' may be used as above to estimate the acoustic attenuation occurring within the patient between the corresponding body-parts (hereinafter, referred to as partial acoustic attenuation). Particularly, the partial acoustic attenuation ΔAtt is simply given by the difference between the measurement power levels ΓPLm and ΓPLm' (i.e., ΔAtt=ΓPLm−ΓPLm'). For example, in this case the partial acoustic attenuation of 1 cm of the organ at issue is equal to ΔAtt=25.3−25=0.3 dB.

The above-described technique according to an embodiment of the present disclosure allows determining the actual (total/partial) acoustic attenuation that occurs in-situ with a high accuracy; this result may be achieved even in in-vivo conditions, in a non-invasive and remote way.

The estimate of the acoustic attenuation occurring in the patient so obtained may be used in diagnostic applications (for example, to characterize the body-part according to its acoustic attenuation).

Figure 7:
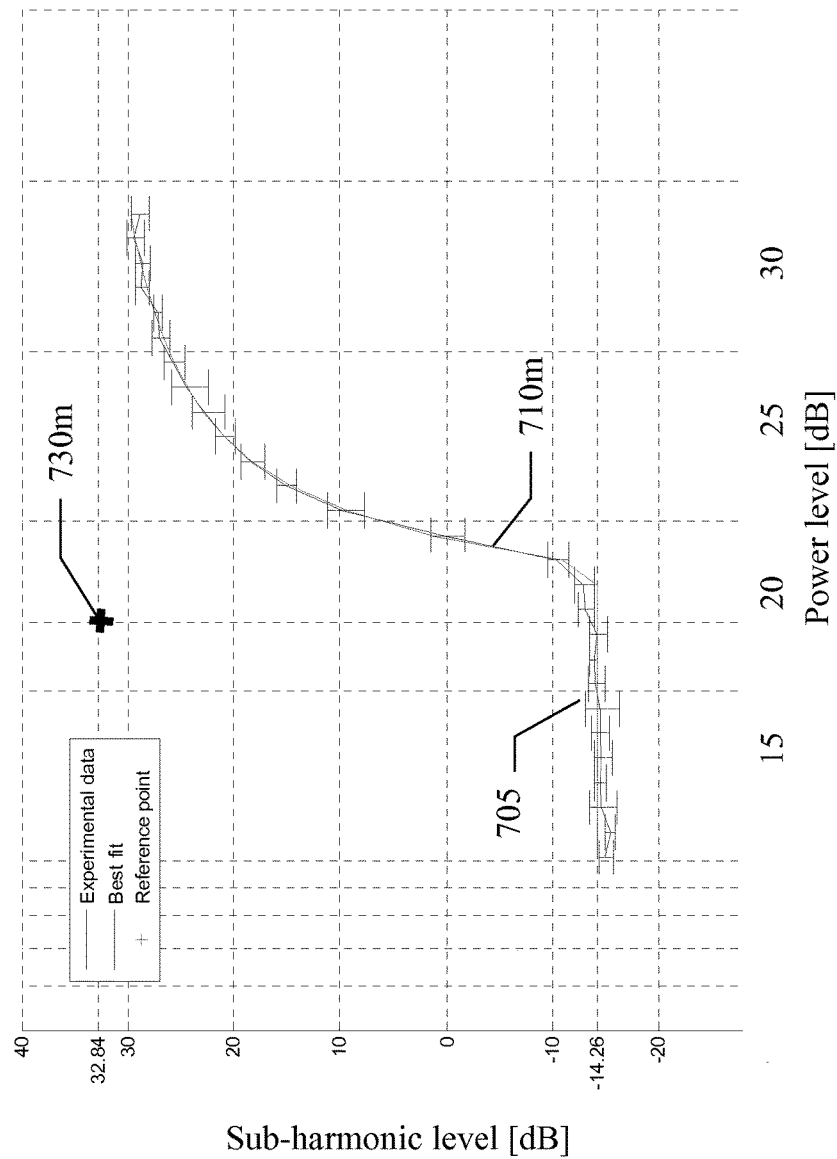
FIG. 7 shows an example of application of the solution according to a further embodiment of the present disclosure.

With reference now to the FIG. 7, an example is shown of application of the solution according to a further embodiment of the present disclosure.

In this case, the measurement excitation signal (used to record the measurement response) is generated by varying the power level of the ultrasound scanner over time in a limited measurement range, which substantially corresponds to the destructive portion of the measurement response; for this purpose, the power level of the ultrasound scanner is varied over time only above a corresponding threshold (for example, above 20 dB, and preferably above 23 dB). A measurement response 705 (substantially limited to its destructive portion) is recorded in response to this measurement excitation signal. The measurement response 705 is fitted by a measurement function (substantially limited to its destructive segment) that is represented by a corresponding (measurement) curve 710*m* with a measurement point represented by a (measurement) cross 730*m*. However, in this case the measurement function is an instance of a simplified model function. For example, the model function may comprise the terms defining the noise segment and the destructive segment only, as defined by the following expression:

$$SH(PL) = 10 \cdot \log\left(10^{\left(\frac{\Gamma SH}{10}\right)} \cdot e^{\left(\frac{-10^{\left(\frac{Kd}{10}\right)} \cdot 10^{\left(\frac{\Gamma PL}{20}\right)}}{PL-10^{\left(\frac{\Gamma PL}{20}\right)}}\right)} + 10^{\left(\frac{Kn}{10}\right)}\right).$$

This reduces the computational complexity of the fitting; moreover, it allows applying the same technique even with a limited dynamic range of the ultrasound scanner. In any case, the loss of accuracy involved by the simplified model function is not substantial, since the most important part of the measurement response for its comparison with the reference response (i.e., the destructive portion) is always taken into account.

Figure 8:
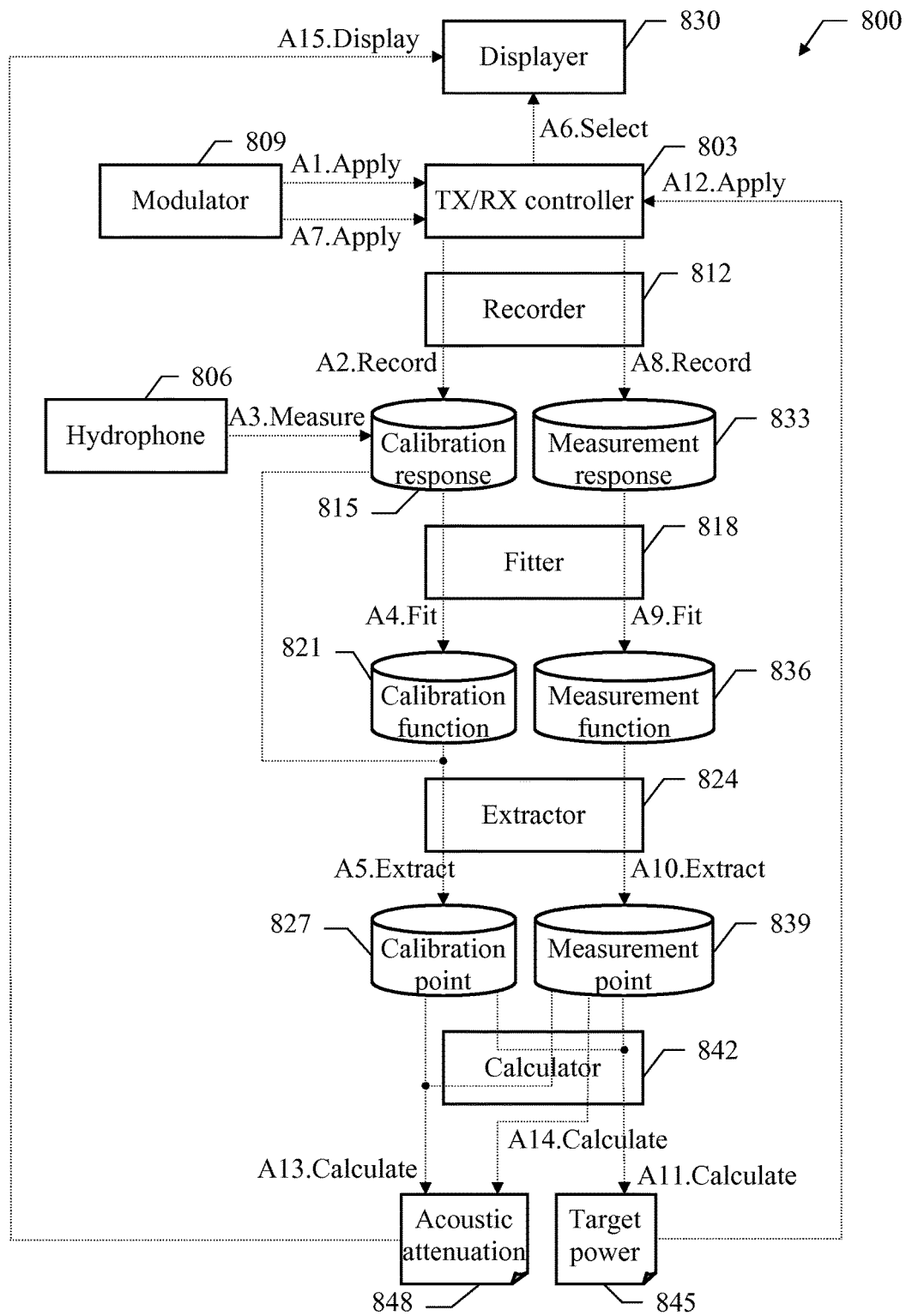
FIG. 8 shows a collaboration diagram representing the roles of the main components that may be used to implement the solution according to an embodiment of the present disclosure.

With reference now to the FIG. 8, a collaboration diagram is shown representing the roles of the main components that may be used to implement the solution according to an embodiment of the present disclosure. These (software and/or hardware) components are denoted as a whole with the reference 800. Particularly, the software components (programs and data) are typically stored in the mass memory and loaded (at least partially) into the working memory of the ultrasound scanner when the programs are running, together with an operating system and other application programs (not shown in the figure). The programs are initially installed into the mass memory, for example, from removable storage units or from a network. In this respect, each software component may represent a module, segment or portion of code, which comprises one or more executable instructions for implementing the specified logical function. Particularly, the figure describes both the static structure of the components 800 and their dynamic behavior (by means of a series of exchanged messages, each one representing a corresponding action, denoted with sequence numbers preceded by the symbol "A").

A TX/RX controller 803 controls the transducer. For example, the TX/RX controller 803 comprises a TX controller with a transmit beam former and pulsers for generating the ultrasound waves at each acquisition instant. The TX/RX controller 803 further comprises a RX processor for receiving the corresponding (analog RF) echo signals at each acquisition instant (for corresponding locations in the selected scan plane). The RX processor pre-amplifies the analog RF echo signals and applies a preliminary time-gain compensation (TGC); the analog RF echo signals are then converted into digital values by an Analog-to-Digital Converter (ADC), and combined into focused beam signals through a receive beam former. The digital RF echo signals so obtained are preferably processed through further digital algorithms and other linear or non-linear signal conditioners (for example, a post-beam-forming TGC). The TX/RX controller 803 further comprises a video converter that demodulates, log-compresses and scan-converts the digital RF echo signals into a video format, so as to generate an anatomical image for each acquisition instant (comprising a matrix of pixel values based on the echo signals of the corresponding locations).

The ultrasound scanner is initialized (in case of use of the calibration response) whenever a new contrast agent has to be used, the setting of the ultrasound scanner is changed (for example, its frequency) or any part of the ultrasound scanner affecting its operation is replaced (for example, the transducer). In this phase, an operator of the ultrasound scanner prepares the calibration structure for the contrast agent, and connects a hydrophone 806 (associated with the calibration structure) to the ultrasound scanner. The operator then places the transducer in contact with the calibration structure and s/he enters an initialization command. In response thereto, a modulator 809 drives the TX/RX controller 803 to apply the calibration excitation signal to each location of the calibration structure (action "A1.Apply"). The (digital RF) calibration echo signal received in response to the calibration excitation signal for each location is passed to a recorder 812, which band-pass filters it around half the fundamental frequency of the ultrasound waves (of the calibration excitation signal) so as to obtain the corresponding sub-harmonic component. In an embodiment, the calibration excitation signal comprises two bursts of ultrasound pulses with opposite signs, with each pairs of pulses of the two bursts that are transmitted in rapid succession; in this case, two corresponding calibration echo signals are received and summed (before band pass filtering). Therefore, in the sum of the two calibration echo signals resulting from each pair of pulses of the two bursts their linear components (due to the tissue) cancel, whereas their non-linear components (due to the contrast agent that responds differently to positive and negative acoustic pressures of equal amplitude) increase. This significantly reduces any linear component possibly contaminating the sub-harmonic response (and which may not be suppressed by simple band pass filtering), thereby improving a response-to-noise ratio and thus the sensitivity of the technique. For each acquisition instant, the recorder 812 calculates the average of the power of the sub-harmonic components of all the locations (defining the sub-harmonic level of the echo signal for the corresponding power level of the ultrasound scanner). The recorder 812 then saves a record for each acquisition instant, storing the corresponding power level and sub-harmonic level, into a calibration response table 815 (action "A2.Record"). At the same time, the hydrophone 806 measures the acoustic pressure applied to the contrast agent at each acquisition instant, which acoustic pressure is added to the corresponding record of the calibration response table 815 (action "A3.Measure"). In this way, each record of the calibration response table 815 represents a point of the calibration response, as defined by the corresponding pair acoustic pressure/sub-harmonic level (for estimating the acoustic pressure) and/or power level/sub-harmonic level (for estimating the acoustic attenuation). A fitter 818 accesses the calibration response table 815. The fitter 815 fits the points of its calibration response by an instance of the model function (for example, by applying well-known error-minimization algorithms) so as to obtain the corresponding calibration function. The fitter 818 saves the values of the parameters defining the calibration function (i.e., Kd, $\Gamma AP/\Gamma PL$, $\Gamma SH$, Kn and possibly Ks, $\Delta AP/\Delta PL$, $\Delta SH$) into a calibration function table 821 (action "A4.Fit"). An extractor 824 accesses the calibration function table 821 and the calibration response table 815 to extract the calibration acoustic pressure $\Gamma APc$ and/or the calibration power level $\Gamma PLc$ (as defined by the value of the parameter $\Gamma PL$ or $\Gamma AP$, respectively, of the calibration function from the calibration function table 821 or in the corresponding record from the calibration response table 815); the extractor 824 saves one or both of these values defining the calibration point into a calibration point variable 827 (action "A5.Extract"). It should be noted that the above-described operations may be performed everywhere (for example, in a laboratory), and that the corresponding components are not required during the actual operation of the scanner.

At the beginning of any treatment/analysis process, the operator actuates the transducer and moves it around the body-part to be treated/analyzed (before administering any contrast agent) and s/he enters a selection command. In response thereto, the TX/RX controller 803 applies ultrasound waves to the body-part (with a relatively low power level) and generates a corresponding sequence of anatomical images in real-time; the anatomical images are provided to a displayer 830, which controls the monitor of the ultrasound scanner so as to cause their display; the operator chooses a scan plane representing a specific slice of the body-part (and possibly a region of interest thereof, selected in an arbitrarily-chosen anatomical image) comprising a known lesion to be treated or a suspected lesion to be analyzed (action "A6.Select"). The operator now administers the contrast agent to the patient, and then s/he enters a treatment command or an analysis command. In case of the treatment command the operator also enters the target acoustic pressure APt to be applied to the body-part. In case of the analysis command the operator also selects whether s/he desires to estimate the total acoustic attenuation (from the transducer to a given depth chosen by the operator in this scan plane) or the partial acoustic attenuation (between two depths within this scan plane, chosen by the operator as well). In response thereto, the modulator 809 drives the TX/RX controller 803 to apply the measurement excitation signal to each location of the body-part, which measurement excitation signal may comprise two bursts of ultrasound pulses with opposite signs as above (action "A7.Apply"). The (digital RF) (measurement) echo signal received in response to the measurement excitation signal is passed to the recorder 812, which generates the corresponding measurement response as above; the recorder 812 then saves a representation of the measurement response into a measurement response table 833, which comprises a record for each acquisition instant storing the corresponding power level of the ultrasound scanner and sub-harmonic level of the echo signal (action "A8.Record"). The fitter 818 accesses the measurement response table 833 and it calculates the corresponding measurement function as above; the fitter 818 saves the values of the parameters defining the measurement function (i.e., Kd, $\Gamma PL$, $\Gamma SH$, Kn and possibly Ks, $\Delta PL$, $\Delta SH$) into a measurement function table 836 (action "A9.Fit"). The extractor 824 accesses the measurement function table 836 to extract the measurement power level $\Gamma PLm$ (as defined by the value of the parameter $\Gamma PL$ of the measurement function), and it saves this value defining the measurement point into a measurement point variable 839 (action "A10.Extract"). In case of estimation of the partial acoustic attenuation, the same operations (actions A8-A10) are reiterated to save the further measurement power level $\Gamma PLm'$ (for the different depth) into the same measurement point variable 839 (in addition to the measurement power level $\Gamma PLm$).

A calculator 842 accesses the calibration point variable 827 and the measurement point variable 839 (to extract the required parameters defining the calibration point and the measurement point, respectively) and it calculates the information of interest for the specific therapeutic/diagnostic application.

Particularly, in case of the treatment command the calculator 842 retrieves the measurement power level $\Gamma PLm$ (from the measurement point variable 839) and the calibration acoustic pressure APc (from the calibration point variable 827), and it calculates the target power level PLt corresponding to the target acoustic pressure APt (previously entered by the operator). The calculator 842 saves the target power level PLt into a target power variable 845 (action "A11.Calculate"). The target power level PLt is then passed from the target power variable 845 to the TX/RX controller 803 so as to cause it to apply the ultrasound waves at the target power level PLt to the body-part ("A12.Apply").

Alternatively, in case of the analysis command based on the total acoustic attenuation the calculator 842 retrieves the measurement power level ΓPLm (from the measurement point variable 839) and the calibration power level ΓPLc (from the calibration point variable 827), and it calculates the corresponding total acoustic attenuation Att. The calculator 842 saves the total acoustic attenuation Att into an attenuation variable 848 (action "A13.Calculate"). Likewise, in case of the analysis command based on the partial acoustic attenuation the calculator 842 retrieves the two measurement power levels ΓPLm and ΓPLm' (from the measurement point variable 839), and it calculates the corresponding partial acoustic attenuation ΔAtt. The calculator 842 saves the partial acoustic attenuation ΔAtt into the same attenuation variable 848 (action "A14.Calculate").

The (total/partial) acoustic attenuation Att/ΔAtt is then passed from the attenuation variable 848 to the displayer 830 that controls the monitor of the ultrasound scanner to display it (action "A15.Display"). For example, this information may be used to characterize the body-part (i.e., to detect a lesion and its type).

With reference now to the FIG. 9-FIG. 13, different examples are shown of experimental results relating to in-vitro applications of the solution according to an embodiment of the present disclosure.

For this purpose, a water tank with a size of 37 cm×57 cm×22 cm was used; the water tank was filled with a suspension in water of a contrast agent comprising BR38 phospholipid microbubbles. The water tank was provided with a custom-built measurement cell and a transducer holder inside it (for a transducer comprising a transmitter and a receiver). The cavity of the measurement cell was 80 mm in diameter and 20 mm in depth, and it had a volume of 130 mL. A small stirrer inside the measurement cell allowed a continuous mixing of the suspension of the contrast agent. The transmitter was a Panametrics 5 MHz transducer, 1 inch in diameter, focused at 3 inches, model V307, serial n° 265437 (Olympus NDT, Waltham, Mass.); the receiver was a Vernon M3 W1001, centered at 3 MHz, 1 inch in diameter, focused at 3 inches (Vernon SA, Tours, France). The transducers were placed at 90° with respect to their longitudinal axes, with both transducers confocally aligned on a bead in pulse-echo mode. The ultrasound waves were provided by a waveform generator Lecroy ArbStudio (Teledyne LeCroy, Chestnut Ridge, N.Y.) and amplified through an RF power amplifier ENI model 3200L (ENI, Rochester, N.Y.) of 55 dB with a serial resistance of 470Ω on input, acting as a −15 dB attenuator. The corresponding echo signals were amplified by an Accutron +40 dB RF amplifier and recorded with a Yokogawa oscilloscope model DL1740 (Yokogawa Electric Corporation, Tokyo, Japan). A proportional valve (T2000, Marsh Bellofram, Newell, W.Va.), connected to a compressed air network and controlled by an electrical set point from the waveform generator, was used to pressurize the measurement cell in a programmable way. A medical pressure probe COBE 041-500-503 (COBE, Lakewood, Colo.) and a custom converter/transmitter device were used to monitor and transmit the hydrostatic pressure signal to the oscilloscope. A custom-made Labview application (National Instrument, Austin, Tex.) controlled the waveform generator and the oscilloscope.

Experimental results were collected in different experimental conditions. The experimental results of each experimental condition were obtained by measuring the sub-harmonic responses for different values of an experimental parameter (with the measure of the sub-harmonic response for each value of the same experimental parameter that was repeated 5 times); the sub-harmonic responses were fitted by corresponding instances of the above-mentioned model function, so as to obtain the characteristic acoustic pressure ΓAP of the corresponding characteristic points. The experimental results of each experimental condition are shown in a diagram that plots the characteristic acoustic pressure ΓAP on the ordinate axis against the values of the corresponding experimental parameter on the abscissa axis (with an error bar indicating the standard deviation of the characteristic acoustic pressures ΓAP for each value of the experimental parameter).

Figure 9:
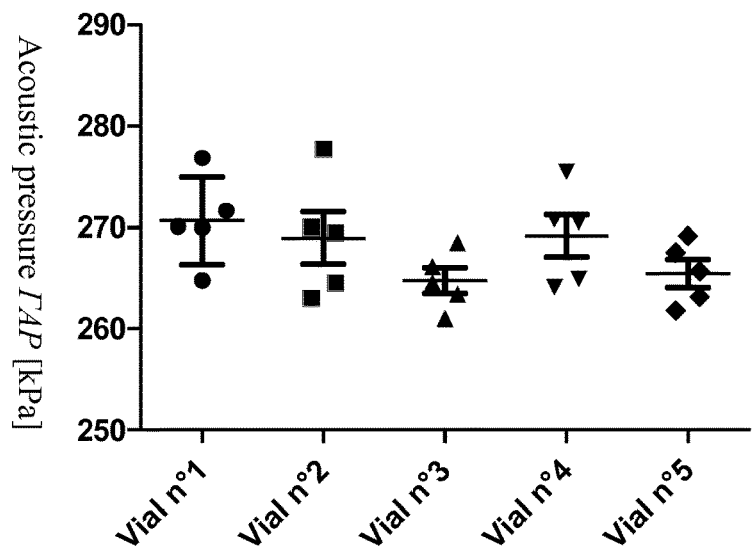
FIG. 9-FIG. 13 show different examples of experimental results relating to in-vitro applications of the solution according to an embodiment of the present disclosure.

Starting from the FIG. 9, the experimental results relate to a contrast agent of the same type coming from 5 different vials (and then with some differences in properties of the contrast agent, such as a size distribution of its particles, due to their intrinsic spread).

Figure 10:
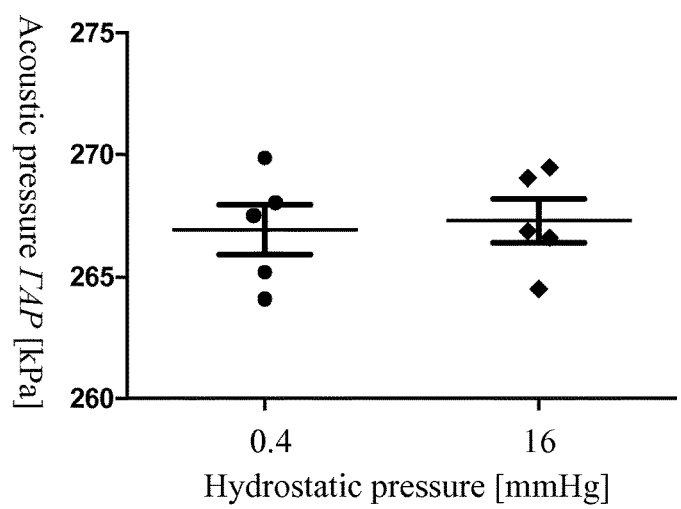

Moving to the FIG. 10, the experimental results relate to different hydrostatic pressures, i.e., 3 mmHg and 120 mmHg (which cover the typical range of systemic pressures observed in the human body).

As may be seen, there is no significant difference in the characteristic acoustic pressure ΓAP for the different contrast agent properties and hydrostatic pressures. This demonstrates a good independence of the technique according to the present disclosure from any spread of the contrast agent properties and from the actual hydrostatic pressure in the patient. Therefore, the technique is highly reproducible, precise and robust.

Figure 11:
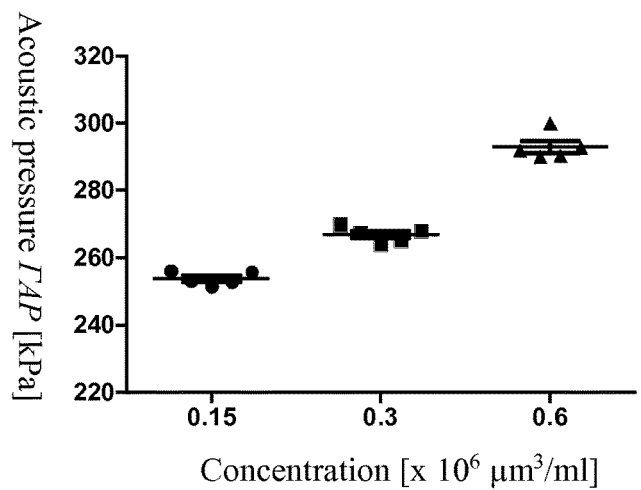

Moving to the FIG. 11, the experimental results relate to different concentrations of the contrast agent, i.e., a standard value thereof ($0.3 \cdot 10^6$ μm$^3$/mL), one half the standard value ($0.15 \cdot 10^6$ μm$^3$/mL), and twice the standard value ($0.6 \cdot 10^6$ μm$^3$/mL). As may be seen, the characteristic acoustic pressure ΓAP increases with the concentration of the contrast agent (since it acts as an acoustic attenuator whose effect increases with the concentration of the contrast agent).

Figure 12:
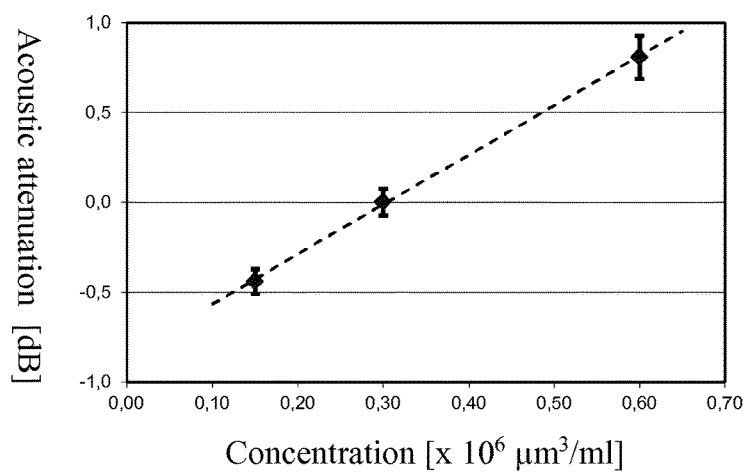

Moving to the FIG. 12, the same experimental results are now shown in a diagram that plots the (relative) acoustic attenuation (in dB, with respect to the characteristic acoustic pressure ΓAP for the standard concentration of the contrast agent) on the ordinate axis against the concentration of the contrast agent on the abscissa axis (with an error bar indicating the standard deviation of the acoustic attenuations for each value of the concentration of the contrast agent). As may be seen, the acoustic attenuation (in dB) is proportional to the concentration of the contrast agent; particularly, a linear best fit of these experimental results has a coefficient of determination $R^2=0.9996$. This confirms a very good match of the technique according to the present disclosure to the theory.

Further experimental results were collected by measuring the sub-harmonic responses without any acoustic attenuator (as indicated above) and then after inserting two pads acting as acoustic attenuators (referred to as pad P1 and pad P2) in the transmission path; particularly, the pad P1 was made of PD442/1.6-di-isocyanatohexane 90.4/9.6% (mass), 50% Bis (2-ethylhexyl)adipate, had a thickness of 9.5 mm and a diameter of 38 mm, whereas the pad P2 was made of PD443/1.6-di-isocyanatohexane 90.5/9.5% (mass), 40% Bis (2-ethylhexyl)adipate, had a thickness of 16 mm and a diameter of 38 mm. The sub-harmonic responses were fitted by corresponding instances of the above-mentioned model function, so as to obtain the characteristic acoustic pressure ΓAP of the corresponding characteristic points.

Figure 13:
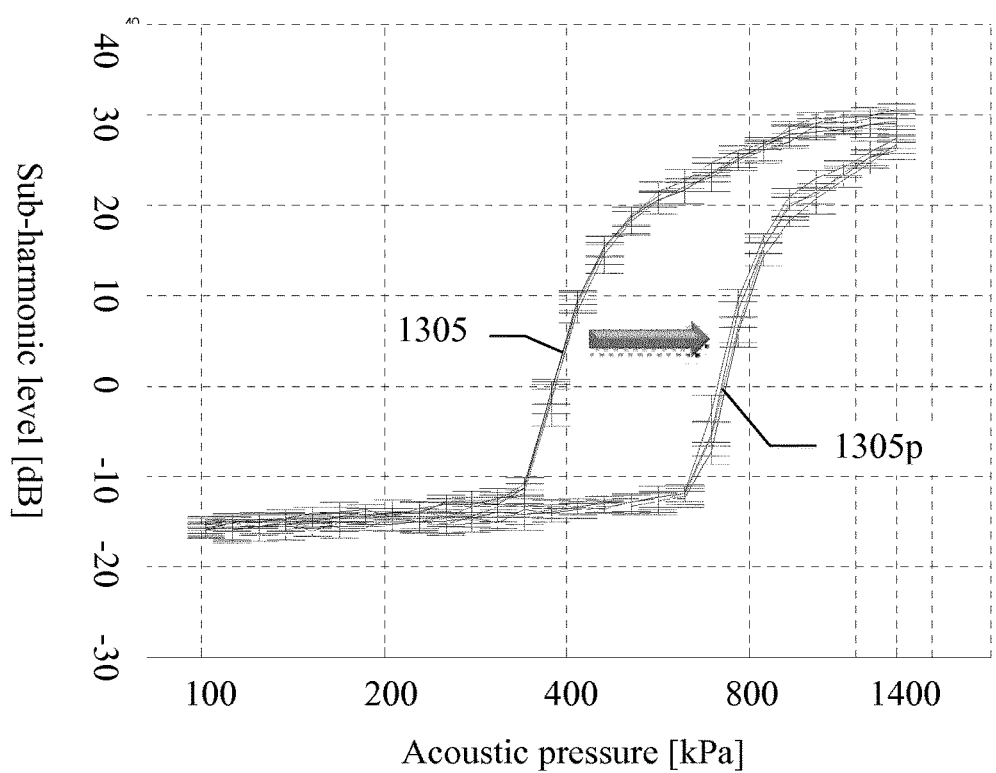

With reference to the FIG. 13, the sub-harmonic response without any acoustic attenuator (denoted with the reference 1305) and the sub-harmonic response with the pad P2 (denoted with the reference 1305p) are shown in a diagram plotting the sub-harmonic level (in dB) on the ordinate axis against the acoustic pressure (in kPa on a logarithmic scale) on the abscissa axis. As may be seen, the destructive portion of the sub-harmonic response 1305p shifts rightwards (because of the increased acoustic attenuation in the transmission path), but without any significant distortion with respect to the pattern of the sub-harmonic response 1305 (similar considerations apply to the sub-harmonic response with the pad P1, not shown in the figure). This confirms that the sub-harmonic response has a substantially constant pattern, irrespectively of the acoustic attenuation.

The acoustic attenuation of each pad P1 and P2, calculated as the ratio (in dB) between the corresponding characteristic acoustic pressure ΓAP and the characteristic acoustic pressure ΓAP without any attenuator, was Att1=2.42 dB and Att2=5.69 dB, respectively. The actual acoustic attenuation of each pad P1 and P2, measured with a standard substitution method using a hydrophone, was Att1'=2.52 dB and Att2'=6.04 dB. This confirms the accuracy of the technique according to the present disclosure.

Naturally, in order to satisfy local and specific requirements, a person skilled in the art may apply many logical and/or physical modifications and alterations to the present disclosure. More specifically, although this disclosure has been described with a certain degree of particularity with reference to one or more embodiments thereof, it should be understood that various omissions, substitutions and changes in the form and details as well as other embodiments are possible. Particularly, different embodiments of the present disclosure may even be practiced without the specific details (such as the numerical values) set forth in the preceding description to provide a more thorough understanding thereof; conversely, well-known features may have been omitted or simplified in order not to obscure the description with unnecessary particulars. Moreover, it is expressly intended that specific elements and/or method steps described in connection with any embodiment of the present disclosure may be incorporated in any other embodiment as a matter of general design choice. In any case, ordinal or other qualifiers are merely used as labels to distinguish elements with the same name but do not by themselves connote any priority, precedence or order. Moreover, the terms include, comprise, have, contain and involve (and any forms thereof) should be intended with an open, non-exhaustive meaning (i.e., not limited to the recited items), the terms based on, dependent on, according to, function of (and any forms thereof) should be intended as a non-exclusive relation (i.e., with possible further variables involved), the term a/an should be intended as one or more items (unless expressly indicated otherwise), and the term means for (or any means-plus-function formulation) should be intended as any entity or structure suitable for carrying out the relevant function.

For example, an embodiment provides a method for use with an ultrasound scanner. The method comprises the following steps. A measurement excitation signal (comprising ultrasound waves generated by varying a power level of the ultrasound scanner in a measurement range) is applied with a transducer of the ultrasound scanner to a body-part of a patient (comprising a contrast agent that has been pre-administered to the patient before performing the method). A measurement response (comprising a level of a non-fundamental component of a measurement echo signal received in response to the measurement excitation signal) is recorded. An estimate value is determined according to a comparison between measurement data (based on the measurement response) and reference data (based on a reference response). Said step of determining an estimate value comprises one or more of the following operations. A target power level (required to apply a selected target acoustic pressure level to the body-part) and/or a further target acoustic pressure level (applied to the body-part when a selected further target power level is set) is estimated when the reference response is a calibration response, which expresses the level of said non-fundamental component of a calibration echo signal as a function of the acoustic pressure level in an in-vitro calibration structure comprising the contrast agent. In addition or in alternative, a total acoustic attenuation (occurring within the patient between the transducer and the body-part) is estimated when the reference response is a further calibration response, which expresses the level of said non-fundamental component of the calibration echo signal as a function of the power level in the in-vitro calibration structure. In addition or in alternative, a partial acoustic attenuation (occurring within the patient between the body-part and a further body-part of the patient) is estimated when the reference response is a further measurement response, which expresses the level of said non-fundamental component of a further measurement echo signal as a function of the power level in the further body-part.

However, the method may be used with any ultrasound scanner (see below). The method may be applied to any body-part, at the level of its entirety, a region of interest thereof, or individually for any location or group of (2D or 3D) locations of the body-part. The body-part may comprise any contrast agent (for example, of target-specific type). The measurement excitation signal may be applied in any way (for example, with ultrasound waves of any shape and length, composed of any number of one or more bursts, each one with any frequency, either constant or increasing/decreasing, or with a mix of different frequencies). The power level of the ultrasound scanner may be defined in any way (for example, by indexes of a graduated scale, by the actual values of the transmission power or the transmission voltage, or even by the actual value of the acoustic pressure of the ultrasound waves that are generated by the ultrasound scanner). Moreover, the power level of the measurement excitation signal may be varied in any way over any non-zero range (for example, with increasing/decreasing ramps). The measurement response may be recorded in any way (for example, by apodizing the echo signal and particularly windowing/tapering it with any kind of function, such as of rectangular, cosine or Hanning type). The level of any non-fundamental component (see below) may be defined in any way (for example, by the power or amplitude of the echo signal). The reference response may be of any type, the measurement data and the reference data may be based on the measurement response and on the reference response, respectively, in any way, and the estimate value may be determined according to any comparison between them (see below). Particularly, the reference response may be defined only as a function of the acoustic pressure level (defined in any way, for example, by its energy over any non-zero range), only as a function of the power level (defined over any non-zero range, even different from the measurement range, and corresponding to the acoustic pressure level in any way, even unknown), or as a function of both of them. The calibration structure and the further body-part may be of any type (see below).

In an embodiment, said step of determining an estimate value comprises estimating the target power level and/or the further target acoustic pressure level further according to a pre-defined relation between the power level and the acoustic pressure level of the ultrasound scanner.

However, the target power level and/or the further target acoustic pressure level may be estimated in any way (see below).

In an embodiment, the method further comprises the following steps. A calibration excitation signal (comprising ultrasound waves generated by varying the power level of the ultrasound scanner in a calibration range) is applied with the transducer to the calibration structure. The level of said non-fundamental component of the calibration echo signal (received in response to the calibration excitation signal) is recorded.

However, any calibration structure (in-vitro) may be used (for example, with a known reflector). Similar considerations are valid for the application of the calibration excitation signal and for the recording of the calibration response (and possibly to the determination of the calibration function and the calibration point) as for the measurement response. In any way, the possibility of providing the calibration data in other ways is not excluded; for example, it is possible to determine (in laboratory or even analytically) the calibration data for a series of different operative conditions (such as settings of the ultrasound scanner and/or types of contrast agent), and then to load this information into the ultrasound scanner. In any case, the calibration response may also be omitted when the further measurement response only is used.

In an embodiment, the method further comprises measuring the acoustic pressure level applied to the contrast agent in the calibration structure by the calibration excitation signal.

However, the acoustic pressure level only, the power level only or both of them may be measured.

In an embodiment, the contrast agent in the calibration structure has a concentration lower than a threshold value providing a substantially null attenuation of the calibration excitation signal and of the calibration echo signal.

However, the attenuation may be deemed null when it is lower than a minimum value (for example, 0.1-1%). In any case, the calibration response may also be recorded with different concentrations of the contrast agent (in attenuation conditions as well).

In an embodiment, the method further comprises the following steps. The further measurement excitation signal is applied with the transducer to the further body-part. The level of said non-fundamental component of the further measurement echo signal (received in response to the further measurement excitation signal) is recorded.

However, similar considerations are valid for the application of the further measurement excitation signal and for the recording of the further measurement response (and possibly for the determination of the further measurement function and the further measurement point) as for the measurement response. Moreover, the further measurement response may be recorded at any time (either concurrently or separately from the measurement response) from any number and type of further body-parts (for example, at any depth in the same organ or even in different organs). In any case, the further measurement response may also be omitted when the calibration response only is used.

In an embodiment, said step of determining an estimate value comprises fitting the measurement response by a measurement function, and determining the estimate value according to a comparison between the measurement function and a reference function fitting the reference response.

However, the measurement response may be fitted by the measurement function with any known curve-fitting algorithm (for example, based on least squares, moments or maximum likelihood techniques). The measurement function may be of any type (for example, a sigmoid or a cumulative lognormal function), even not known a priori. The measurement function and the reference function may be compared in any way (see below). In any case, the possibility of comparing the measurement response with the reference function or with the reference response directly (even without calculating any measurement function) is not excluded in principle (for example, according to an average of the difference between the destructive portions of the measurement response and of the reference response).

In an embodiment, the measurement function and the reference function are instances of a model function with a generic S-shape; the model function comprises a final constant segment with a substantially constant final value, a further constant segment with a substantially constant further value, and an increasing segment between the further constant segment and the final constant segment wherein the model function increases substantially monotonically from the further constant value to the final constant value.

However, each segment of the model function may have any non-zero length. The (final/further) constant segments may have any constant values, which values may be deemed substantial constant when their change is lower than a pre-defined threshold (for example, 0.1-1%); moreover, the increasing segment may be of any type (for example, strictly or weakly increasing, with any number and type of concavities). In any case, the use of a model function with a different shape is not excluded.

In en embodiment, the model function further comprises an initial constant segment with a substantially initial value, and a further increasing segment between the initial constant segment and the further constant segment wherein the model function increases substantially monotonically from the initial constant value to the further constant value.

However, similar considerations as above apply to the initial constant segment and to the further increasing segment. In any case, the model function may comprise different, additional or alternative segments.

More generally, the model function may relate to any other portion of the measurement/reference responses (at least comprising their destructive portion or a substantial part thereof, for example, above the transition power level); for example, the model function may span from all the segments indicated above down to the increasing segment only.

In an embodiment, said step of determining an estimate value comprises determining a measurement point being characteristic of the increasing segment of the measurement function, and determining the estimate value according to a comparison between the measurement point and a reference point being characteristic of the increasing segment of the reference function.

However, the measurement point may be determined in any way (see below); moreover, the reference point may be defined by the reference acoustic pressure level only, the reference power level only or both of them. The measurement point and the reference point may be compared in any way (see below). In any case, the possibility of comparing the measurement point with the reference function or the measurement function with the reference function directly (even without determining any measurement point) is not excluded in principle (for example, according to an average of the difference between the increasing segments of the measurement function and of the reference function).

In an embodiment, said step of determining an estimate value comprises determining the measurement point in correspondence to an intersection between the further constant segment and the increasing segment of the measurement function, and determining the estimate value according to a comparison between the measurement point and the reference point in correspondence to an intersection between the further constant segment and the increasing segment of the reference function.

However, the measurement/reference points may be defined in any other way, even independently of the intersection between the further constant segment and the increasing segment (for example, as the points wherein the first derivative of the increasing segment has a pre-defined value, such as 1).

In an embodiment, said step of determining an estimate value comprises determining the measurement point in correspondence to a descending vertical asymptote of the increasing segment, and determining the estimate value according to a comparison between the measurement point and the reference point in correspondence to a descending vertical asymptote of the increasing segment of the reference function.

However, the measurement/reference points may be determined in any other way according to the intersection between the further constant segment and the increasing segment (for example, where the two segments actually intersect).

In an embodiment, the reference point is a calibration point (which is characteristic of the increasing segment of a calibration function fitting the calibration response); said step of estimating the target power level and/or the further target acoustic pressure level comprises estimating the target power level and/or the further target acoustic pressure level by applying the pre-defined relation between the power level and the acoustic pressure level of the ultrasound scanner to a measurement power level (identified by the measurement point) and a calibration acoustic pressure level (identified by the calibration point).

However, the target power level and/or the further target pressure level may be calculated with any other formula (according to any relation of the ultrasound scanner, either known analytically or determined experimentally).

In an embodiment, the reference point is a further calibration point, which is characteristic of the increasing segment of a further calibration function fitting the further calibration response; said step of estimating a total acoustic attenuation comprises estimating the total acoustic attenuation according to a comparison between a measurement power level (identified by the measurement point) and a calibration power level (identified by the further calibration point).

However, the total acoustic attenuation may be calculated according to any comparison between the measurement power level and the calibration power level (for example, their difference, ratio, even not in logarithmic scale) and it may be expressed in any way (for example, in absolute terms to indicate the actual loss of acoustic pressure).

In an embodiments, the reference point is a further measurement point, which is characteristic of the increasing segment of a further measurement function fitting the further measurement response; said step of estimating a partial acoustic attenuation comprises estimating the partial acoustic attenuation according to a comparison between a measurement power level (identified by the measurement point) and a further measurement power level (identified by the further measurement point).

However, the partial acoustic attenuation may be calculated according to any comparison between the two measurement power levels and it may be expressed in any way as above.

In an embodiment, the body-part and the further body-part are at different depths in the patient from a skin thereof.

However, the two body-parts may be at any different depths; in any case, the estimation of the partial acoustic attenuation between different organs (even at the same depth) is not excluded.

In an embodiment, said non-fundamental component is a sub-harmonic component of the echo signal.

However, the use of different, alternative or additional non-fundamental components (or any combination thereof) is not excluded; for example, nothing prevents using higher harmonic components (such as the $2^{nd}$ or $3^{rd}$ harmonics) or ultra-harmonic components (such as with a frequency equal to 1.5 or 2.5 the fundamental frequency).

In an embodiment, said sub-harmonic component is equal to ½ a fundamental frequency of the echo signal.

However, the use of any different, alternative or additional sub-harmonic components (or any combination thereof) is not excluded (for example, equal to ⅓ or ¼ the fundamental frequency).

In an embodiment, said step of applying a measurement excitation signal comprises applying a first measurement excitation signal and a second measurement excitation signal opposite the first measurement excitation signal; said step of recording a measurement response comprises recording a first measurement response in response to the first measurement excitation signal and a second measurement response in response to the second measurement excitation signal, and obtaining the measurement response according to a combination of the first measurement response and the second measurement response.

However, the measurement response may be obtained with any multi-pulse excitation technique. Particularly, the measurement excitation signals may be of any type (for example, with different amplitude) and they may be applied in any way (for example, in succession or interleaved); moreover, the corresponding measurement responses may be combined in any way (for example, by adding or subtracting them, either directly or with corresponding weights). In any case, a basic implementation based on a single-pulse excitation technique (i.e., with the measurement excitation signal composed of a single burst of ultrasound pulses) is not excluded.

In an embodiment, the method further comprises controlling the ultrasound scanner according to the target power level.

However, in a simplified implementation the target power level may be simply displayed to the operator that sets the ultrasound scanner accordingly in a manual way.

Generally, similar considerations apply if the same solution is implemented with an equivalent method (by using similar steps with the same functions of more steps or portions thereof, removing some steps being non-essential, or adding further optional steps); moreover, the steps may be performed in a different order, concurrently or in an interleaved way (at least in part).

In any case, it is emphasized that the above-described method is a data processing (or computational) method that may be implemented independently of any interaction with the patient (and particularly with the contrast agent that may be pre-administered thereto before performing the method). Moreover, the contrast agent may also be administered to the patient in a non-invasive manner (for example, orally for imaging the gastro-intestinal tract or via a nebulizer into the airways), or in any case without any substantial physical intervention thereon that would require professional medical expertise or entail any health risk for the patient (for example, intramuscularly). In any case, although the proposed method may facilitate the task of a physician, it generally only provides intermediate results that may help him/her in controlling a treatment of the body-part in therapeutic applications and/on in analyzing the body-part in diagnostic applications (even though the decision of the treatment for therapeutic purposes and/or the diagnosis for curative purposes stricto sensu are always made by the physician himself/herself).

A further embodiment provides a computer program, which is configured for causing a computing system to perform the above-mentioned method when the computer program is executed on the computing system.

A further embodiment provides a computer program product, which comprises a computer readable storage medium embodying a computer program; the computer program is loadable into a working memory of a computing system thereby configuring the computing system to perform the same method.

However, the same solution may be implemented as a stand-alone module, as a plug-in for a control program of the ultrasound scanner, or even directly in the control program itself; it would be readily apparent that it is also possible to deploy the same solution as a service that is accessed through a network (such as in the Internet). In any case, similar considerations apply if the software program (which may be used to implement each embodiment of the present disclosure) is structured in a different way, or if additional modules or functions are provided; likewise, the memory structures may be of other types, or may be replaced with equivalent entities (not necessarily consisting of physical storage media). The program may take any form suitable to be used by any data-processing or computing system or in connection therewith (for example, within a virtual machine), thereby configuring the system to perform the desired operations; particularly, the program may be in the form of external or resident software, firmware, or microcode (either in object code or in source code—for example, to be compiled or interpreted). Moreover, it is possible to provide the program on any computer-usable medium (and particularly as an article of manufacture on a non-transitory medium); the medium may be any element suitable to contain, store, communicate, propagate, or transfer the program. For example, the medium may be of the electronic, magnetic, optical, electromagnetic, infrared, or semiconductor type; examples of such medium are fixed disks (where the program may be pre-loaded), removable disks, tapes, cards, wires, fibers, wireless connections, networks, broadcast waves, and the like. In any case, the solution according to an embodiment of the present invention lends itself to be implemented even with a hardware structure (for example, integrated in a chip of semiconductor material), or with a combination of software and hardware suitably programmed or otherwise configured.

A further embodiment provides a system, which comprises means configured for performing the steps of the above-mentioned method.

However, the ultrasound scanner may be of any type (for example, with a transducer of the linear, convex or phased type). Moreover, the same solution may be applied in a system comprising an ultrasound scanner and a distinct computer (or any equivalent system); in this case, the recorded information is transferred from the ultrasound scanner to the computer for its processing (for example, through a digital, analogue or network connection).

Generally, similar considerations apply if the system has a different structure or comprises equivalent components, or it has other operative characteristics. In any case, every component thereof may be separated into more elements, or two or more components may be combined together into a single element; moreover, each component may be replicated to support the execution of the corresponding operations in parallel. Moreover, unless specified otherwise, any interaction between different components generally does not need to be continuous, and it may be either direct or indirect through one or more intermediaries.

A further embodiment provides a therapeutic method comprising the following steps. A contrast agent is administered to a patient to cause the contrast agent to perfuse a body-part of the patient. A measurement excitation signal, comprising ultrasound waves generated by varying a power level of an ultrasound scanner in a measurement range, is applied with a transducer of the ultrasound scanner to the body-part. A measurement response, comprising a level of a non-fundamental component of a measurement echo signal received in response to the measurement excitation signal, is recorded (with the measurement response that is processed according to the above-mentioned method to estimate said target power level required to apply the selected target acoustic pressure level to the body-part). Further ultrasound waves generated by setting the power level of the ultrasound scanner according to said target power level are applied to the body-part.

However, the obtained information may be used in any way. For example, it is possible to use the contrast agent as target for heat deposition so as to heat the body-part; moreover, it is possible to use a contrast agent that is functionalized with a drug and destroy its particles to cause the delivery of the drug in-situ (with the measurement response that is recorded using the same contrast agent being non-functionalized). The same method may find application in any kind of therapeutic applications (in the broadest meaning of the term—for example, aimed at curing a pathological condition, at avoiding its progress, at preventing the occurrence of a pathological condition, or simply at ameliorating a comfort of the patient) and for treating any kind of body-part (for example, organs, such as liver, prostate or heart, regions or tissues) of any (human or animal) patient.

A further embodiment provides a diagnostic method comprising the following steps. A contrast agent is administered to a patient to cause the contrast agent to perfuse a body-part of the patient. A measurement excitation signal, comprising ultrasound waves generated by varying a power level of an ultrasound scanner in a measurement range, is applied with a transducer of the ultrasound scanner to the body-part. A measurement response, comprising a level of a non-fundamental component of a measurement echo signal received in response to the measurement excitation signal, is recorded (with the measurement response that is processed according to the above-mentioned method to estimate said total acoustic attenuation occurring within the patient between the transducer and the body-part and/or said partial acoustic attenuation occurring within the patient between the body-part and the further body-part of the patient). A health condition of the body-part is evaluated according to the total acoustic attenuation and/or the partial acoustic attenuation.

However, the obtained information may be used in any way (for example, by estimating the (total/partial) acoustic attenuation of each location, or group of adjacent locations, of the body-part and then generating a parametric image with each pixel value thereof that represents the acoustic attenuation of the corresponding location). The same method may find application in any kind of diagnostic applications (in the broadest meaning of the term—for example, aimed at either discovering new lesions or monitoring known lesions) and for analyzing any kind of body-part of any patient (see above).

The invention claimed is:

1. A method for use with an ultrasound scanner, the method comprising:
applying a measurement excitation signal, comprising ultrasound waves generated by varying a power level of the ultrasound scanner in a measurement range, with a transducer of the ultrasound scanner to a body-part of a patient comprising a contrast agent being pre-administered to the patient before performing the method,
recording a measurement response comprising a level of a non-fundamental component of a measurement echo signal received in response to the measurement excitation signal, and
determining an estimate value according to a comparison between measurement data based on the measurement response and reference data based on a reference response, said determining an estimate value being implemented by any one or more of the following steps:
a1) estimating a target power level required to apply a selected target acoustic pressure level to the body-part further according to a pre-defined relation between the power level and the acoustic pressure level of the ultrasound scanner when the reference response is a calibration response expressing the level of said non-fundamental component of a calibration echo signal as a function of the acoustic pressure level in an in-vitro calibration structure comprising the contrast agent,
a2) estimating a further target acoustic pressure level applied to the body-part when a selected further target power level is set further according to a pre-defined relation between the power level and the acoustic pressure level of the ultrasound scanner when the reference response is a calibration response expressing the level of said non-fundamental component of a calibration echo signal as a function of the acoustic pressure level in an in-vitro calibration structure comprising the contrast agent,
b) estimating a total acoustic attenuation occurring within the patient between the transducer and the body-part when the reference response is a further calibration response expressing the level of said non-fundamental component of the calibration echo signal as a function of the power level in the in-vitro calibration structure, and
c) estimating a partial acoustic attenuation occurring within the patient between the body-part and a further body-part of the patient when the reference response is a further measurement response expressing the level of said non-fundamental component of a further measurement echo signal as a function of the power level in the further body-part.

2. The method according to claim 1, comprising:
applying a calibration excitation signal, comprising ultrasound waves generated by varying the power level of the ultrasound scanner in a calibration range, with the transducer to the calibration structure, and
recording the level of said non-fundamental component of the calibration echo signal received in response to the calibration excitation signal.

3. The method according to claim 2, comprising:
measuring the acoustic pressure level applied to the contrast agent in the calibration structure by the calibration excitation signal.

4. The method according to claim 2, wherein the contrast agent in the calibration structure has a concentration lower than a threshold value providing a substantially null attenuation of the calibration excitation signal and of the calibration echo signal.

5. The method according to claim 1, comprising:
applying a further measurement excitation signal with the transducer to the further body-part, and
recording the level of said non-fundamental component of the further measurement echo signal received in response to the further measurement excitation signal.

6. The method according to claim 1, wherein said determining an estimate value comprises:
fitting the measurement response by a measurement function, and
determining the estimate value according to a comparison between the measurement function and a reference function fitting the reference response.

7. The method according to claim 6, wherein the measurement function and the reference function are instances of a model function with a generic S-shape, the model function comprising a final constant segment with a substantially constant final value, a further constant segment with a substantially constant further value, and an increasing segment between the further constant segment and the final constant segment wherein the model function increases substantially monotonically from the further constant value to the final constant value.

8. The method according to claim 7, wherein the model function further comprises an initial constant segment with a substantially initial value, and a further increasing segment between the initial constant segment and the further constant segment wherein the model function increases substantially monotonically from the initial constant value to the further constant value.

9. The method according to claim 7, wherein said determining an estimate value comprises:
determining a measurement point being characteristic of the increasing segment of the measurement function, and
determining the estimate value according to a comparison between the measurement point and a reference point being characteristic of the increasing segment of the reference function.

10. The method according to claim 9, wherein said determining an estimate value comprises:
determining the measurement point in correspondence to an intersection between the further constant segment and the increasing segment of the measurement function, and determining the estimate value according to a comparison between the measurement point and the reference point in correspondence to an intersection between the further constant segment and the increasing segment of the reference function.

11. The method according to claim 10, wherein said determining an estimate value comprises:
determining the measurement point in correspondence to a descending vertical asymptote of the increasing segment of the measurement function, and
determining the estimate value according to a comparison between the measurement point and the reference point in correspondence to a descending vertical asymptote of the increasing segment of the reference function.

12. The method according to claim 9, wherein the reference point is a calibration point being characteristic of the increasing segment of a calibration function fitting the calibration response, said determining an estimate value comprising:
estimating the target power level and/or the further target acoustic pressure level by applying the pre-defined relation between the power level and the acoustic pressure level of the ultrasound scanner to a measurement power level identified by the measurement point and a calibration acoustic pressure level identified by the calibration point.

13. The method according to claim 9, wherein the reference point is a further calibration point being characteristic of the increasing segment of a further calibration function fitting the further calibration response, said estimating a total acoustic attenuation comprising:
estimating the total acoustic attenuation according to a comparison between a measurement power level identified by the measurement point and a calibration power level identified by the further calibration point.

14. The method according to claim 9, wherein the reference point is a further measurement point being characteristic of the increasing segment of a further measurement function fitting the further measurement response, said estimating a partial acoustic attenuation comprising:
estimating the partial acoustic attenuation according to a comparison between a measurement power level identified by the measurement point and a further measurement power level identified by the further measurement point.

15. The method according to claim 1, wherein the body-part and the further body-part are at different depths in the patient from a skin thereof.

16. The method according to claim 1, wherein said non-fundamental component is a sub-harmonic component of the echo signal.

17. The method according to claim 16, wherein said sub-harmonic component is equal to ½ a fundamental frequency of the echo signal.

18. The method according to claim 1, wherein said applying a measurement excitation signal comprises:
applying a first measurement excitation signal and a second measurement excitation signal opposite the first measurement excitation signal, and wherein said recording a measurement response comprises:
recording a first measurement response in response to the first measurement excitation signal and a second measurement response in response to the second measurement excitation signal and obtaining the measurement response according to a combination of the first measurement response and the second measurement response.

19. The method according to claim 1, comprising:
controlling the ultrasound scanner according to the target power level.

20. A computer program product comprising a non-transitory computer readable storage medium embodying a computer program, the computer program being loadable into a working memory of a computing system thereby configuring the computing system to perform a method for use with an ultrasound scanner, the method comprising:
applying a measurement excitation signal, comprising ultrasound waves generated by varying a power level of the ultrasound scanner in a measurement range, with a transducer of the ultrasound scanner to a body-part of a patient comprising a contrast agent being pre-administered to the patient before performing the method,
recording a measurement response comprising a level of a non-fundamental component of a measurement echo signal received in response to the measurement excitation signal, and
determining an estimate value according to a comparison between measurement data based on the measurement response and reference data based on a reference response, said determining an estimate value comprising any one or more of:
a1) estimating a target power level required to apply a selected target acoustic pressure level to the body-part further according to a pre-defined relation between the power level and the acoustic pressure level of the ultrasound scanner when the reference response is a calibration response expressing the level of said non-fundamental component of a calibration echo signal as a function of the acoustic pressure level in an in-vitro calibration structure comprising the contrast agent,
a2) estimating a further target acoustic pressure level applied to the body-part when a selected further target power level is set further according to a pre-defined relation between the power level and the acoustic pressure level of the ultrasound scanner when the reference response is a calibration response expressing the level of said non-fundamental component of a calibration echo signal as a function of the acoustic pressure level in an in-vitro calibration structure comprising the contrast agent,
b) estimating a total acoustic attenuation occurring within the patient between the transducer and the body-part when the reference response is a further calibration response expressing the level of said non-fundamental component of the calibration echo signal as a function of the power level in the in-vitro calibration structure, and
c) estimating a partial acoustic attenuation occurring within the patient between the body-part and a further body-part of the patient when the reference response is a further measurement response expressing the level of said non-fundamental component of a further measurement echo signal as a function of the power level in the further body-part.

21. A system for use with an ultrasound scanner, the system comprising:
a circuit for applying a measurement excitation signal, comprising ultrasound waves generated by varying a power level of the ultrasound scanner in a measurement range, with a transducer of the ultrasound scanner to a body-part of a patient comprising a contrast agent being pre-administered to the patient,
a circuit for recording a measurement response comprising a level of a non-fundamental component of a measurement echo signal received in response to the measurement excitation signal, and a circuit for determining an estimate value according to a comparison between measurement data based on the measurement response and reference data based on a reference response, said circuit for determining an estimate value comprising one or more of the following circuits:

a1) a circuit for estimating a target power level required to apply a selected target acoustic pressure level to the body-part further according to a pre-defined relation between the power level and the acoustic pressure level of the ultrasound scanner when the reference response is a calibration response expressing the level of said non-fundamental component of a calibration echo signal as a function of the acoustic pressure level in an in-vitro calibration structure comprising the contrast agent, a2) a circuit for estimating a further target acoustic pressure level applied to the body-part when a selected further target power level is set further according to a pre-defined relation between the power level and the acoustic pressure level of the ultrasound scanner when the reference response is a calibration response expressing the level of said non-fundamental component of a calibration echo signal as a function of the acoustic pressure level in an in-vitro calibration structure comprising the contrast agent, b) a circuit for estimating a total acoustic attenuation occurring within the patient between the transducer and the body-part when the reference response is a further calibration response expressing the level of said non-fundamental component of the calibration echo signal as a function of the power level in the in-vitro calibration structure, and c) a circuit for estimating a partial acoustic attenuation occurring within the patient between the body-part and a further body-part of the patient when the reference response is a further measurement response expressing the level of said non-fundamental component of a further measurement echo signal as a function of the power level in the further body-part.

22. A therapeutic method comprising:

administering a contrast agent to a patient to cause the contrast agent to perfuse a body-part of the patient, applying a measurement excitation signal, comprising ultrasound waves generated by varying a power level of an ultrasound scanner in a measurement range, with a transducer of the ultrasound scanner to the body-part, recording a measurement response comprising a level of a non-fundamental component of a measurement echo signal received in response to the measurement excitation signal, a target power level required to apply a selected target acoustic pressure level to the body-part being estimated according to a comparison between measurement data based on the measurement response and reference data based on a calibration response expressing the level of said non-fundamental component of a calibration echo signal as a function of the acoustic pressure level in an in-vitro calibration structure comprising the contrast agent and according to a pre-defined relation between the power level and the acoustic pressure level of the ultrasound scanner, and applying further ultrasound waves, generated by setting the power level of the ultrasound scanner according to said target power level, to the body-part.

23. A diagnostic method comprising:

administering a contrast agent to a patient to cause the contrast agent to perfuse a body-part of the patient, applying a measurement excitation signal, comprising ultrasound waves generated by varying a power level of an ultrasound scanner in a measurement range, with a transducer of the ultrasound scanner to the body-part, recording a measurement response comprising a level of a non-fundamental component of a measurement echo signal received in response to the measurement excitation signal, a total acoustic attenuation occurring within the patient between the transducer and the body-part being estimated according to a comparison between measurement data based on the measurement response and reference data based on a calibration response expressing the level of said non-fundamental component of the calibration echo signal as a function of the power level in an in-vitro calibration structure comprising the contrast agent, and evaluating a health condition of the body-part according to the total acoustic attenuation.

24. An ultrasound scanner comprising the system of claim 21.

25. A diagnostic method comprising:

administering a contrast agent to a patient to cause the contrast agent to perfuse a body-part of the patient, applying a measurement excitation signal, comprising ultrasound waves generated by varying a power level of an ultrasound scanner in a measurement range, with a transducer of the ultrasound scanner to the body-part, recording a measurement response comprising a level of a non-fundamental component of a measurement echo signal received in response to the measurement excitation signal, a partial acoustic attenuation occurring within the patient between the body-part and a further body-part of the patient being estimated according to a comparison between measurement data based on the measurement response and reference data based on a further measurement response expressing the level of said non-fundamental component of a further measurement echo signal as a function of the power level in the further body-part, and evaluating a health condition of the body-part according to the partial acoustic attenuation.

* * * * *